US012434015B2

(12) United States Patent
Fenster et al.

(10) Patent No.: US 12,434,015 B2
(45) Date of Patent: Oct. 7, 2025

(54) AUTOINJECTOR

(71) Applicant: AMGEN INC., Thousand Oaks, CA (US)

(72) Inventors: Valerie M. Fenster, Woodland Hills, CA (US); Stephanie Toy, Cincinnati, OH (US); Mark Ka Lai Lee, Newbury Park, CA (US); Denise Meyer, Sudbury, MA (US)

(73) Assignee: AMGEN INC., Thousand Oaks, CA (US)

(*) Notice: Subject to any disclaimer, the term of this patent is extended or adjusted under 35 U.S.C. 154(b) by 680 days.

(21) Appl. No.: 16/531,654

(22) Filed: Aug. 5, 2019

(65) Prior Publication Data

US 2019/0351152 A1 Nov. 21, 2019

Related U.S. Application Data

(63) Continuation of application No. 14/434,347, filed as application No. PCT/US2013/065798 on Oct. 18, 2013, now Pat. No. 10,398,854.

(Continued)

(51) Int. Cl.

*A61M 5/42* (2006.01)
*A61M 5/20* (2006.01)

(Continued)

(52) U.S. Cl.

CPC .............. *A61M 5/425* (2013.01); *A61M 5/20* (2013.01); *A61M 5/3205* (2013.01);

(Continued)

(58) Field of Classification Search

CPC ...... A61M 5/425; A61M 5/20; A61M 5/3205; A61M 5/5086; A61M 5/2033;

(Continued)

(56) References Cited

U.S. PATENT DOCUMENTS 4,955,871 A * 9/1990 Thomas ................ A61M 5/282 222/215
5,226,893 A 7/1993 Kayser (Continued)

FOREIGN PATENT DOCUMENTS

CN 1917912 A 2/2007
JP 2007-514489 A 6/2007

(Continued)

OTHER PUBLICATIONS

Chinese Patent Application No. 201380054262.X, Notification of the Fourth Office Action, dated Dec. 11, 2018.

(Continued)

*Primary Examiner* — Alireza Nia
*Assistant Examiner* — Hamza A Darb
(74) *Attorney, Agent, or Firm* — MARSHALL, GERSTEIN & BORUN LLP

(57) ABSTRACT

An injector such as a needle-type autoinjector having a flexible flange disposed at an injection end of the injector for stretching or pinching the skin of the injection site. The flexible flange may be removably attached to the injector or integrated into the injector during manufacturing. Further, an injector having a palm button disposed at an activation end of the injector for activating an injection cycle of the injector. The palm button may be removably attached to the injector or integrated into the injector during manufacturing. Still further, a holding device for one-handed operation of an injector, the holding device having a sleeve and at least one hand rest coupled to the sleeve, the sleeve and hand rest providing ergonomic holding and operation of the injector. Still further, autoinjector needle shield having an enlarged, rounded lip for contacting the skin at the injection site.

16 Claims, 22 Drawing Sheets

Related U.S. Application Data

(60) Provisional application No. 61/716,425, filed on Oct. 19, 2012.

(51) Int. Cl.
*A61M 5/32* (2006.01)
*A61M 5/50* (2006.01)

(52) U.S. Cl.
CPC ......... *A61M 5/5086* (2013.01); *A61M 5/2033* (2013.01); *A61M 5/2046* (2013.01); *A61M 2005/206* (2013.01); *A61M 2005/2073* (2013.01); *A61M 2005/208* (2013.01); *A61M 5/322* (2013.01); *A61M 5/326* (2013.01); *A61M 2205/583* (2013.01); *A61M 2205/586* (2013.01)

(58) Field of Classification Search
CPC .... A61M 5/2046; A61M 5/322; A61M 5/326; A61M 2005/206; A61M 2005/2073; A61M 2005/208; A61M 2205/583; A61M 2205/586; A61M 5/3243; A61M 5/42; A61M 2005/2026; A61M 2005/3264; A61M 2005/3139; A61M 5/3137; A61M 5/31526
See application file for complete search history.

(56) References Cited

U.S. PATENT DOCUMENTS

| | | | | |
|---|---|---|---|---|
| 6,099,504 | A | 8/2000 | Gross et al. | |
| 6,102,896 | A | 8/2000 | Roser | |
| 6,152,332 | A | 11/2000 | Funk | |
| 6,537,242 | B1 | 3/2003 | Palmer | |
| 7,377,903 | B2 | 5/2008 | Raney | |
| 10,398,854 | B2 * | 9/2019 | Fenster | A61M 5/425 |
| 2003/0093032 | A1 | 5/2003 | Py et al. | |
| 2003/0229308 | A1 | 12/2003 | Tsals et al. | |
| 2007/0021716 | A1 | 1/2007 | Hansen | |
| 2007/0211716 | A1 * | 9/2007 | Oz | H04L 63/0272 370/389 |
| 2007/0270768 | A1 * | 11/2007 | Dacquay | A61M 5/1452 604/272 |
| 2008/0195056 | A1 | 8/2008 | Bishop et al. | |
| 2009/0270804 | A1 | 10/2009 | Mesa et al. | |
| 2010/0036320 | A1 * | 2/2010 | Cox | A61M 5/31541 604/135 |
| 2010/0113981 | A1 | 5/2010 | Oki et al. | |
| 2011/0022006 | A1 | 1/2011 | Walters et al. | |
| 2011/0092915 | A1 * | 4/2011 | Olson | A61M 5/2033 604/198 |
| 2011/0144584 | A1 | 6/2011 | Wozencroft | |
| 2012/0046615 | A1 | 2/2012 | Koiwai et al. | |
| 2012/0179113 | A1 | 7/2012 | Yokota et al. | |
| 2012/0253314 | A1 * | 10/2012 | Harish | A61M 5/3287 434/262 |
| 2013/0263997 | A1 | 10/2013 | Down et al. | |
| 2014/0296782 | A1 * | 10/2014 | Ulrich | A61M 5/3232 604/173 |

FOREIGN PATENT DOCUMENTS

| | | | |
|---|---|---|---|
| JP | 2011-530361 | | 12/2011 |
| JP | 2011-530361 | A | 12/2011 |
| NZ | 260359 | | 7/1998 |
| NZ | 260359 | A | 7/1998 |
| WO | 95/01198 | | 1/1995 |
| WO | WO-95/01198 | A1 | 1/1995 |
| WO | 01/93931 | | 12/2001 |
| WO | WO-01/93931 | A1 | 12/2001 |
| WO | 2010/018411 | | 2/2010 |
| WO | WO-2010/018411 | A1 | 2/2010 |
| WO | 2011094025 | | 8/2011 |
| WO | WO-2011094025 | A1 | 8/2011 |
| WO | 2012/127366 | | 9/2012 |
| WO | WO-2012/127366 | A1 | 9/2012 |
| WO | 2012/135537 | | 10/2012 |
| WO | WO-2012/135537 | A2 | 10/2012 |

OTHER PUBLICATIONS

Examination Report No. 1 issued in counterpart Australian Patent Application No. 2013331015, dated Jul. 22, 2017.
Israeli Patent Application No. 238229, Office Action, dated Oct. 23, 2018.
Japanese patent application No. 2015-538094, Decision of Rejection and Decision to Reject the Amendments, dated Oct. 22, 2018.
Notice of Reasons for Rejection mailed on Jul. 31, 2017 in counterpart Japanese Patent Application No. 2015-538094, and translation thereof.
Notice of Reasons for Rejection mailed on Mar. 19, 2018 in counterpart Japanese Patent Application No. 2015-538094, and translation thereof.
Notification of the Third Office Action, Chinese Application No. 201380054262.X, State Intellectual Property Office of The People's Republic of China, dated Nov. 10, 2017.
Rejection Decision mailed on Apr. 3, 2013 in counterpart Chinese Patent Application No. 201380054262.X, and translation thereof.
Canadian Patent Application No. 2888788, Office Action, dated Jun. 19, 2019.
Japanese Patent Application No. 2015-538094, Notice of Allowance, dated May 27, 2019.
European Patent Application No. 13846664.4, European Search Report, dated May 18, 2016.
Chinese Patent Application No. 201380054262.X, Notification of the Fifth Office Action, dated Jun. 14, 2019.
U.S. Office Action for U.S. Appl. No. 14/434,347, dated Mar. 22, 2018.
U.S. Office Action for U.S. Appl. No. 14/434,347, dated Mar. 30, 2017.
U.S. Office Action for U.S. Appl. No. 14/434,347, dated Oct. 2, 2017.
U.S. Office Action for U.S. Appl. No. 14/434,347, dated Dec. 16, 2016.
Chinese Application for Invention No. 202010098112.0, First Office Action, dated Jul. 1, 2021.
Japanese Patent Application No. 2019-029299, Notice of Reasons for Rejection, mailed Jan. 14, 2020.

* cited by examiner

AUTOINJECTOR

CROSS-REFERENCE TO RELATED APPLICATIONS

This is a continuation of U.S. patent application Ser. No. 14/434,347, filed Apr. 8, 2015, now U.S. Pat. No. 10,398,854 B2, issued on Sep. 3, 2019, which is the U.S. National Stage of International Patent Application No. PCT/US13/65798, filed Oct. 18, 2013, which claims the priority benefit of U.S. Provisional Application No. 61/716,425, filed Oct. 19, 2012. The entirety of the foregoing is expressly incorporated herein by reference.

FIELD

The present disclosure relates to autoinjector devices. More particularly, the present disclosure relates to an autoinjector device having a skin stretching and pinching capability, an ergonomic autoinjector holding device, and other ergonomic improvements for autoinjectors.

BACKGROUND

Autoinjector (AI) devices are held against the body while an injection needle pierces the skin to administer a drug product. While gripping the AI, the user applies a downward movement against the skin that activates the AI. The user then presses a button to cause the needle to inject and the stopper to move the drug downward into the skin.

During needle insertion and plunger movement, the interface/surface area between the user's skin and the AI's physical area touching the skin (and encompassing the needle) must remain in place to avoid AI and/or needle slippage or movement on the surface of the skin. This must occur to enable a full drug dose delivery, to avoid drug leakage on the skin's surface, and most importantly, to avoid user injury from a bent or broken needle during the injection process. Additionally, for user comfort, it is advised that the injection site's skin area, and directly under the AI, be kept taut to facilitate the injection procedure.

Today's AI procedures advise users to stretch or pinch the skin at the injection site with one hand and to maintain that stretch or pinch while placing the AI over the same area. With the AI in place, the user applies a downward force on the site area to activate or unlock the device. While keeping the skin stretched or pinched with one hand and the AI gripped in position with the other, the user must then use the thumb of the hand holding the AI to depress a button located at the top of the AI, thereby, activating needle and plunger downward movement to inject the drug. After the injection is completed, the needle may be retracted from the skin and the user lifts off the device.

During the act of placing and activating the AI onto the site, users have been observed to: 1) lose concentration, letting go of the stretched or pinched skin, and attempting to maneuver the AI into place; 2) let go of the stretched or pinched skin in order to grip the AI with two hands due to their lack of physical hand strength or dexterity; and 3) lift the device off too soon before the injection is complete. Further, the use of AIs can be a significant challenge for seniors or finger function compromised users and consequently, treatment can be hindered.

Hence, there are multiple considerations for the front wall at the injection end of the AI. One such consideration is the AI's ability to stretch skin. The user is not expected to stretch the skin while injecting with the AI, therefore, it would be very beneficial to have a feature on the AI that will provide this function. Another consideration is to provide the AI with a feature that improves the stability of the AI, so that it remains approximately perpendicular to the body during injection, thereby allowing the user to operate the AI with one hand. Still another consideration is that some commercial AIs require the application of an axial force to a trigger release mechanism on the front wall of the AI where it contacts the user's skin. Some body types have lower surface tension and resistance to the required activation force thereby causing the AI to press against the skin and deflect into the body a significant amount. Some patients do not apply the required activation force thereby not allowing the AI to arm and be ready to inject. Some commercial AIs have a shield trigger and activation button which must be pressed to arm and initiate delivery. Other commercial AIs only require a shield trigger to be pressed to arm and initiate delivery.

Accordingly, methods are needed which solve the placement, activation, and ergonomic design issues of conventional AIs.

SUMMARY

An injector comprising a housing having an injection end, an injection needle enclosed within the housing, the injection needle penetrating skin at a selected injection site and dispensing a drug product when an injection cycle of the injector is activated, and a flexible extension disposed at the injection end of the housing for stretching or pinching the skin of the injection site.

In some embodiments of the injector, the flexible extension may be integral with the housing.

In some embodiments of the injector, the flexible extension may be removably attached to the housing.

Some embodiments of the injector may further comprise a locking arrangement for removably attaching the flexible extension to the housing, the locking arrangement including interlocking first and second members, the flexible extension including one of the first and second members and the housing including the other one of the first and second members.

In some embodiments of the injector, the flexible extension may be selected from a kit of flexible extensions, wherein one of the flexible extensions of the kit may be constructed to stretch the skin of the injection site and wherein another one of the flexible extensions of the kit may be constructed to pinch the skin of the injection site.

In some embodiments of the injector, the flexible extension is non-removably attached to the housing of the injector.

Some embodiments of the injector may further comprise an adaptor for attaching to a housing of the injector, wherein the flexible extension may be removably attached to the adaptor.

Some embodiments of the injector may further comprise a locking arrangement for removably attaching the flexible extension to the adaptor, the locking arrangement including interlocking first and second members, the flexible extension including one of the first and second members and the adaptor including the other one of the first and second members.

In some embodiments of the injector, the flexible extension is constructed as a flange.

In some embodiments of the injector, the flexible extension is made of a polyurethane or silicon-polyurethane copolymer material.

Some embodiments of the injector may further comprise a needle shield for covering the injection needle upon withdrawal of the injection needle from the skin of the injection site.

In some embodiments of the injector, the flexible extension may be integral with the needle shield.

In some embodiments of the injector, the flexible extension may be removably attached to the needle shield.

In some embodiments of the injector, the needle shield may be colored for indicating completion of the injection cycle.

Some embodiments of the injector may further comprise a soft guard attached to the needle shield, the guard for preventing the needle shield from contacting the skin at the injection site.

In some embodiments of the injector, the flexible extension may have one or more ring-shaped protrusions or ridges formed in or on a working surface of the extension.

In some embodiments of the injector, the flexible extension may have a plurality of nubs formed in or on a working surface of the extension.

In some embodiments of the injector, the flexible extension may have a grippy or textured working surface.

Some embodiments of the injector may further comprise a palm button device for at least activating the injection cycle of the injector.

In some embodiments of the injector, the palm button device may have a mushroom shaped palm button.

In some embodiments of the injector, the palm button device may have a handle shaped palm button.

In some embodiments of the injector, the palm button device may comprise a palm button having at least one indent for placement of a user's thumb.

In some embodiments of the injector, the palm button may have a polyurethane gel elastomer coating.

In some embodiments of the injector, the palm button device may be integral with the injector.

In some embodiments of the injector, the palm button device may be removably attached to the housing of the injector.

In some embodiments of the injector, the palm button device may be non-removably attached to the housing of the injector.

In some embodiments of the injector, the palm button device may comprise a palm button and a mounting arrangement for operatively coupling the palm button to the injector.

In some embodiments of the injector, the mounting arrangement may comprise a base extending from the palm button and an adaptor for attaching to a housing of the injector, wherein the base is movably coupled to the adaptor.

Some embodiments of the injector may further comprise a holding device for aiding a user in the operation of the injector, the holding device comprising a sleeve for ergonomically holding and operating the injector with one hand and at least one hand rest extending out from the sleeve for maintaining a user's hand on the sleeve when holding and operating the injector.

In some embodiments of the injector, the sleeve of the holding device may have a polyurethane gel elastomer layer that defines a hand grip.

In some embodiments of the injector, the sleeve may have a top wall operative as stop for properly positioning the sleeve on the injector so that a user can operate the injector with one hand.

In some embodiments of the injector, the top wall may include an opening for allowing an activation button of the injector to extend through the top wall.

In some embodiments of the injector, the at least one hand rest may pivotally couple to the sleeve.

In some embodiments of the injector, the at least one hand rest may include a projection that engages a side wall of the housing if the at least one hand rest is in a clamping position, thereby removably attaching the holding device to the injector.

In some embodiments of the injector, the holding device may further comprise a detent arrangement for retaining the at least one hand rest in the clamping position.

In some embodiments of the injector, the at least one hand rest may be contoured to receive the hypothenar muscle area of the user's hand.

In some embodiments, of the injector, the holding device may be integral with the injector.

In some embodiments of the injector, the holding device may be removably attached to the housing of the injector.

In some embodiments of the injector, the holding device may include a locking arrangement for non-removably attaching the holding device to the housing of the injector.

In some embodiments of the injector, the holding device may allow a user to arm and initiate the injection cycle of the injector.

In some embodiments of the injector, the holding device may allow a user to initiate the injection cycle of the injector.

In some embodiments of the injector, the sleeve may be capable of slidably moving on the housing of the injector to initiate the injection cycle of the injector Further, an injector comprising a housing having an activation end and an injection end disposed opposite to and inline with the activation end, and further comprising the earlier described palm button device disposed at the activation end of the housing, wherein the palm button device activates an injection cycle of the injector.

Still further, an injector comprising a housing and the holding device described earlier, for aiding a user in the operation of the injector.

Still further, a skin manipulating device for use with an injector having an injection needle, the device comprising a flexible extension for stretching or pinching skin at the selected injection site.

In some embodiments of the skin manipulating device, the flexible extension may have one or more ring-shaped protrusions or ridges formed in or on a working surface thereof.

In some embodiments of the skin manipulating device, the flexible extension may have a plurality of nubs formed in or on a working surface thereof.

In some embodiments of the skin manipulating device, the flexible extension may have a grippy or textured working surface.

In some embodiments of the skin manipulating device, the flexible extension may be integral with the injector.

In some embodiments of skin manipulating device, the flexible extension may be removably attached to the injector.

In some embodiments of the skin manipulating device, the flexible extension may further comprise an adaptor to be attached to a housing of the injector, the flexible extension being removably attachable to the adaptor.

Some embodiments of the skin manipulating device may further comprise a locking arrangement for removably attaching the flexible extension to the adaptor, the locking arrangement including interlocking first and second members, the flexible extension including one of the first and second members and the adaptor including the other one of the first and second members.

Still further, a holding device for aiding a user in the operation of an injector. The holding device may comprise a sleeve for ergonomically holding and operating the injector with one hand, and at least one hand rest extending out from the sleeve for maintaining a user's hand on the sleeve when holding and operating the injector.

In some embodiments of the holding device, the sleeve may have a polyurethane gel elastomer layer that defines a hand grip.

In some embodiments of the holding device, the sleeve may have a top wall operative as stop for properly positioning the sleeve on the injector so that a user can operate the injector with one hand.

In some embodiments of the holding device, the top wall may include an opening for an activation button of the injector.

In some embodiments of the holding device, the at least one hand rest may be pivotally coupled to the sleeve.

In some embodiments of the holding device, the at least one hand rest may include a projection for engaging a side wall of the housing, if the at least one hand rest is in a clamping position, thereby allowing removable attachment of the holding device to the injector.

Some embodiments of the holding device may further comprise a detent arrangement for retaining the at least one hand rest in the clamping position.

In some embodiments of the holding device, the at least one hand rest may be contoured to receive the hypothenar muscle area of the user's hand.

Some embodiments of the holding device may further comprise a locking arrangement for non-removably attaching the holding device to the housing of the injector.

Some embodiments of the holding device may allow a user to initiate the injection cycle of the injector.

In some embodiments of the holding device, the sleeve may be capable of being slidably moved on the housing of the injector to initiate the injection cycle of the injector.

Still further, a palm button device for at least activating an injection cycle of an injector. The palm button device may comprise a palm button and a mounting arrangement for operatively coupling the palm button to the injector.

In some embodiments of the palm button device, the mounting arrangement may comprise a base extending from the palm button and an adaptor for attaching to a housing of the injector, wherein the base movably coupled to the adaptor.

In some embodiments of the palm button device, the palm button may have a mushroom-shape.

In some embodiments of the palm button device, the palm button may have a handle-shape.

In some embodiments of the palm button device, the palm button may have at least one indent for placement of a user's thumb.

In some embodiments of the palm button device, the palm button may have a polyurethane gel elastomer coating.

In some embodiments of the palm button device, the adaptor may non-removably attach to the housing of the injector.

Some embodiments of the injectors described above may further comprise a container or syringe containing a therapeutic product.

BRIEF DESCRIPTION OF THE DRAWINGS

FIG. 7A illustrates the flattening and radial expansion of the flange as the autoinjector is pressed down by a user during the activation of an injection cycle, thereby spreading or stretching the skin S at the injection site.

FIG. 7B illustrates the flattening and radial expansion of the flange as the autoinjector is pressed down by a user during the activation of an injection cycle, thereby spreading or stretching the skin S at the injection site.

FIG. 7C illustrates the flattening and radial expansion of the flange as the autoinjector is pressed down by a user during the activation of an injection cycle, thereby spreading or stretching the skin S at the injection site.

FIG. 10A illustrates the hand holding device with its hand rests disposed in an up position for packaging and FIG. 10B illustrates the hand holding device affixed to an embodiment of an autoinjector with its hand rests in a down position.

FIG. 10C illustrates the hand rest in an up position and FIG. 10D illustrates the the hand rest in a down position engaging the housing the autoinjector.

FIG. 11A illustrates the hand holding device and FIG. 11B illustrates the hand holding device affixed to an embodiment of an autoinjector.

DETAILED DESCRIPTION

Figure 1A:
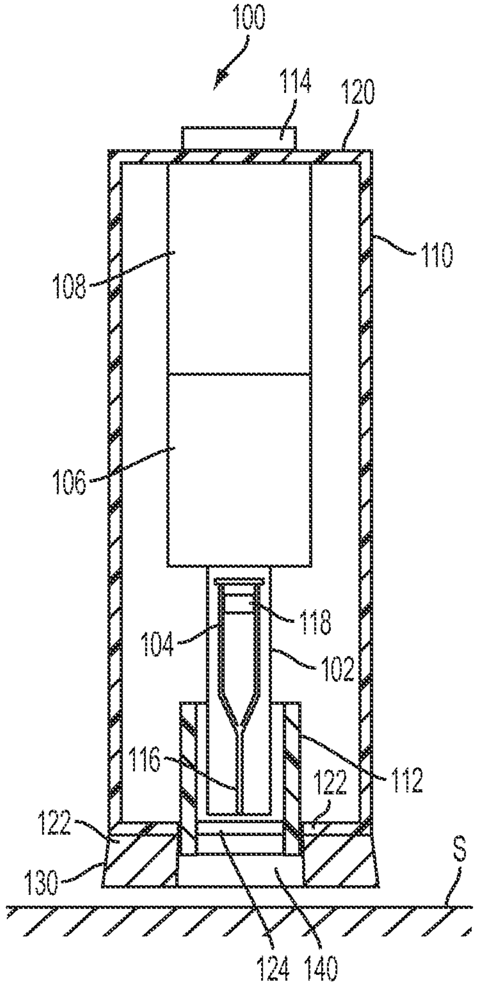
FIG. 1A is a sectional elevation view of an embodiment of a flexible skin manipulating flange removably attached to or integrated with an autoinjector, prior to activation of an injection cycle of the autoinjector.
Figure 1B:
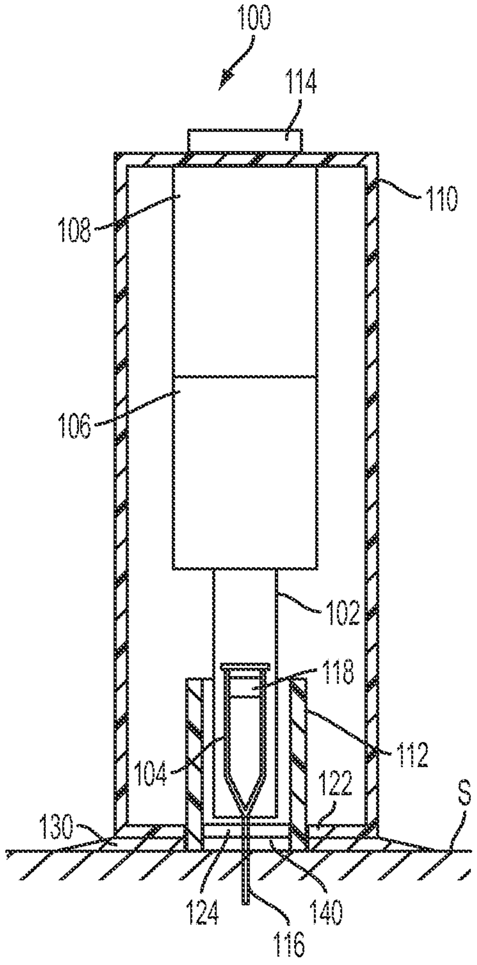
FIG. 1B is a sectional elevation view of the flexible skin manipulating flange and autoinjector of FIG. 1A, illustrating a user pressing the autoinjector down onto the skin at the injection site during an injection cycle of the autoinjector.
Figure 3A:
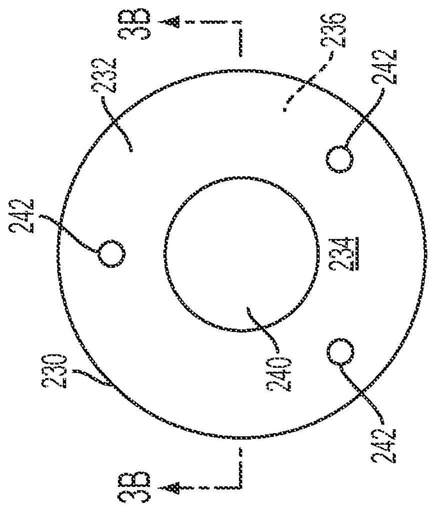
FIG. 3A is an end view of another embodiment of a flexible skin manipulating flange illustrating a surface of the flange which faces the autoinjector.
Figure 3B:
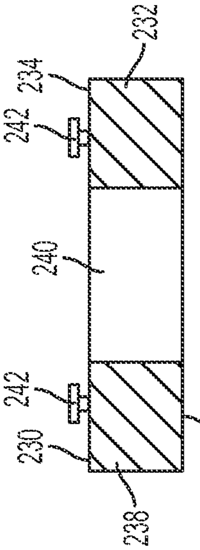
FIG. 3B is a section view through line 3B-3B of the flexible skin manipulating flange illustrated in FIG. 3A.
Figure 2A:
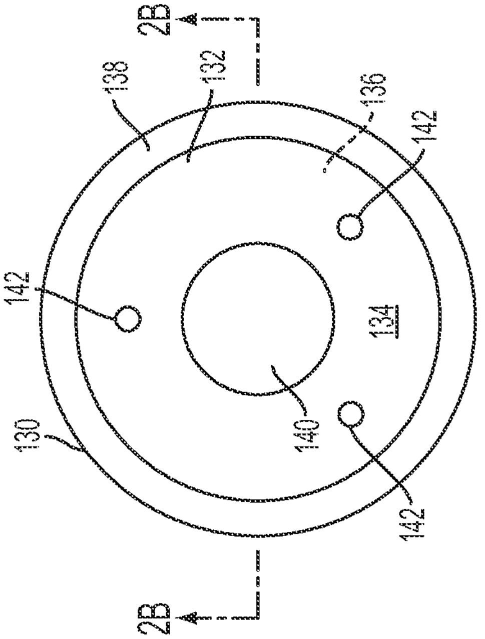
FIG. 2A is an end view of an embodiment of a flexible skin manipulating flange illustrating a surface of the flange which faces the autoinjector.
Figure 2B:
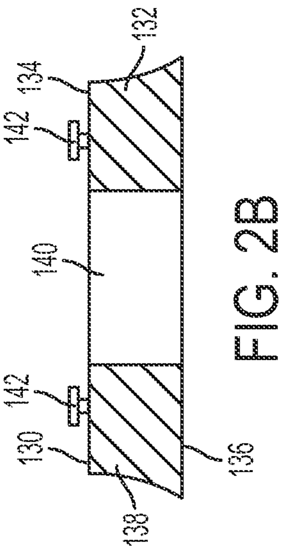
FIG. 2B is a section view through line 2B-2B of the flexible skin manipulating flange illustrated in FIG. 2A.

FIGS. 1A and 1B illustrate an embodiment of a flexible skin manipulating flange-like extension (skin manipulating flange) 130 removably attached to or integrated with an autoinjector (AI) 100 or other body injector. The skin manipulating flange (SMF) 130 increases the surface area of the AI 100 at an injection end thereof and, therefore, provides the AI 100 with a stable platform that discourages device slippage/movement on the skin's surface when the user feels the AI 100 pressed completely down onto the skin. The stable platform provided by the SMF 130 also prevents the user from leaning the AI 100 to the right, left, front or back or moving the AI 100 in circular motion, and thus, aiding the user in keeping the AI 100 at a 90 degree angle to the skin (preferred injection angle). The SMF 130 also facilitates device placement and simplifies the injection procedure by eliminating the skin stretch or pinch step for injection site preparation, thereby allowing the user to freely use either one or two hands to manipulate and stabilize the AI 100, keeps the skin held taut under the AI 100 for user comfort, allows the user in some embodiments to view the injection needle through the SMF material, thereby ensuring visual feedback that the injection needle is in place and/or upon injection completion, the injection needle is retracted. The SMF 130 does not uncomfortably stick to the skin using glue or adhesive backing and can be constructed, shaped, and adapted to accommodate any autoinjector or on body injectors placed onto the skin.

The AI 100 may conventionally comprise a drug product container carrier 102, a container or syringe 104 pre-filled with a fluid-based drug product, a drive unit 106, an activation and drive control unit 108, a housing 110 for enclosing one or more of the drug product container carrier 102, the container 104, the drive unit 106, and the activation and drive control unit 108. The AI 100 may also comprise a needle shield or guard 112 disposed within (as shown) or external to the housing 110. The container or syringe 104 may include an injection needle 116 and a stopper 118 for dispensing the drug product. The container carrier 102 may be configured to receive and hold the container 104 in defined relationship to the housing 110 and be axially movable in relation to the housing 110, for needle penetration purposes, between a rear position and a front position, movement between which positions is used for needle penetration. The housing 110 of the AI 100 may have a first or rear end wall 120 and an opposing second or front end wall 122, which respectively define activation and injection ends of the AI 100. The front end wall 122 may have an injection needle opening 124 that allows the injection needle 116 of the container or syringe 104 to extend therethrough during the operation of the AI 100, as illustrated in FIG. 1B. The drive unit 106 may include an autopenetration mechanism for moving the carrier 102 or container 104 relative to the housing 110 or carrier 102, respectively to insert the injection needle 116 into the skin S. The drive unit 106 may further include an autoinjection mechanism for moving or plunging the stopper 118 through the container or syringe 104 to dispense the drug product, and a needle shield deployment mechanism for deploying the needle shield 112 around the injection needle 116 after completion of the injection. If the AI 100 is not provided with the optional needle shield 112, the autopenetration mechanism may also be configured to automatically withdraw the injection needle 116 back into the housing 110. The various drive unit mechanisms may utilize stored energy in any known form including, without limitation, electrical, mechanical (e.g., elastic member such as springs), gas pressure, gas releasing, and any combination thereof. The stored energy can be transmitted by corresponding conventional transmission mechanisms, e.g. electromechanical, such as electric motors or solenoids, hydraulic, pneumatic, mechanical springs, gears, rods, and the like. The drive control and activation unit may be provided for activating and sequencing the drive mechanisms of the drive unit 106 and may comprise any well know type of a releasable lock arrangements, electronic controllers, combinations thereof, and the like. The activation and drive control unit 108 may be both armed and injection initiated by a button or switch 114 extending though the rear end wall 120 of the housing 110 at the activation end of the AI 100. In other embodiments, the needle shield 112 may extend slightly past the front end wall 122 of the AI housing 110 and be adapted to operate as a trigger to arm the activation and drive control unit 108 when the needle shield 112 is depressed by contact with the skin. In such other embodiments, depression of the activation button 114 would cause the activation and drive control unit 108 to initiate delivery.

The SMF 130 extends the surface area of the injection end (front wall 122) of the AI 100, which comes in contact with the skin S of the injection site during initial activation and/or unlocking. As the user presses downward to arm the AI 100, the SMF 130 gently stretches the skin S taut, and out of the way from the center of the injection site and injection needle 116 of the AI 100.

As collectively illustrated in FIGS. 2A, 2B, 3A, and 3B, the SMF 130, 230 may comprise a flexible, annular body 132, 232 having a first end surface 134, 234, an opposing second end surface 136, 236, a cylindrical side surface 138, 238 extending between the first end surface 134, 234 and the second end surface 136, 236, and an aperture 140, 240 extending through a generally central portion of the body 132, 232. Certain embodiments of the SMF 130, 132 may optionally include protrusions 142, 242 disposed on the first surface 134, 234 thereof, the purpose of which will be explained further on. In some embodiments, the SMF 130, 230 may be made from a flexible material, such as transparent polyurethane or silicone-polyurethane co-polymer, which allows the user to view the injection needle 116 through the SMF 130, 230 during an injection. In other embodiments, the SMF 130, 230 may be made from a translucent or an opaque polyurethane material, a nitrile rubber copolymer material, or any other suitable material capable of flexing. As shown in the embodiment illustrated in FIGS. 2A and 2B, the side surface 138 of the SMF 130 may be constructed to flare outwardly from the first surface 134 to the second surface 136 to allow the SMF 130 to be easily compressed and flattened, as illustrated in FIG. 1B, by pressing the AI 100 down on the skin S at the injection site thereby maximizing radial expansion of the SMF 130, particularly the second surface 136 thereof. As illustrated, in FIGS. 1A and 1B, the aperture 140 of the SMF 132 axially aligns with the injection needle opening 124 formed in the front end wall 122 of the AI housing 110 to allow the injection needle 116 of the container or syringe 104 to extend therethrough during the operation of the AI 100.

In certain embodiments, the SMF may be a separate accessory that a user can removably attach to AI at injection time. In such embodiments, the SMF may be selected from a kit of differently configured SMFs. The kit may be provided with the AI or be available separately for use with the AI. For example but not limitation, one or more of the SMFs may be configured to spread or stretch the skin taut at the injection site while one or more of the other SMFs may be configured to pinch the skin at the injection site. Accordingly, the user can select a desired one of the SMFs in the kit based on whether the user wants a skin pinching or skin spreading effect. In some embodiments, the SMF may be configured to both spread/stretch the skin or pinch the skin at the injection site, depending upon whether the user is pressing the AI down or lifting it up.

Figure 4A:
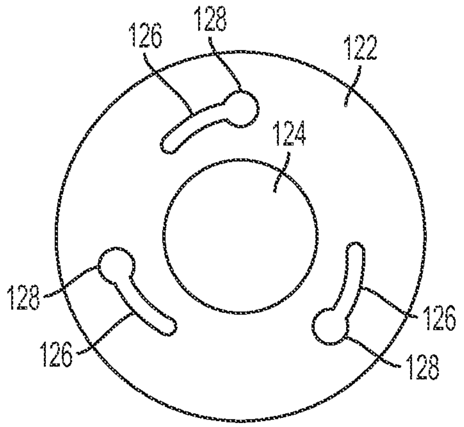
FIG. 4A is an end view of an autoinjector illustrating a surface of the autoinjector's housing which has been adapted to couple a removable variant of a flexible skin manipulating flange.
Figure 4B:
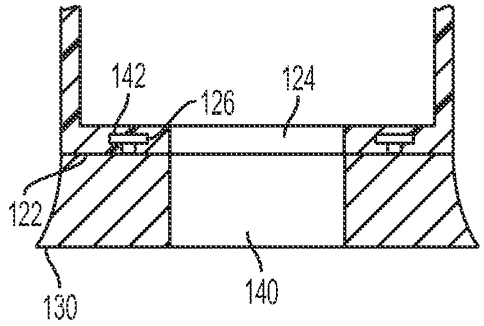
FIG. 4B is a section view of the flexible skin manipulating flange illustrated in FIGS. 2A and 2B removably attached to the surface of the autoinjector's housing illustrated in FIG. 4A.
Figure 4C:
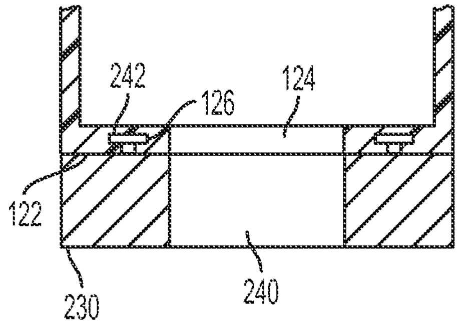
FIG. 4C is a section view of the flexible skin manipulating flange illustrated in FIGS. 3A and 3B removably attached to the surface of autoinjector's housing illustrated in FIG. 4A.

Any suitable coupling arrangement may removably attach the SMF to the AI 100. FIGS. 4A-4C illustrate an embodiment of a twist locking arrangement that may be used for removably attaching the SMF 130, 230 illustrated in FIGS. 2A-2B and FIGS. 3A-3B, to the AI 100. The twist locking arrangement may comprise two or more arcuate slots 126 formed in the front end wall 122 of the AI 100 in, for example, a circularly spaced arrangement. The twist locking arrangement may further comprise a corresponding number of protrusions 142, 242 formed on the first surface 134, 234 of the SMF 130, 230 in, for example, a circularly spaced arrangement. The protrusions 142, 242 of the SMF 130, 230 are configured to slidably move within the arcuate slots 126 formed in the front end wall 122 of the AI 100. Although not illustrated, the two or more arcuate slots may be formed in the first end surface of the SMF and the corresponding number of protrusions may be formed on the front end wall of the AI. The protrusions 142, 242 may have a pin-head configuration or have any other suitable configuration capable of being removably retained in the arcuate slots. One end 128 of each of the arcuate slots 126 may be enlarged for allowing insertion and withdrawal of the pin-head shaped protrusions 142, 242. To attach the SMF 130, 230 to the injection end of the AI 100, the user may insert the protrusions 142, 242 into the enlarged ends 128 of the arcuate slots 126 and twist the SMF 130, 230 in a first direction relative to the AI 100 to lock the SMF 130, 230 on the AI 100. The SMF 130, 230 may be removed from the AI 100 by twisting the SMF 130, 230 relative to the AI 100 in a second direction and then separating the SMP 130, 230 from the AI 100.

Figure 4D:
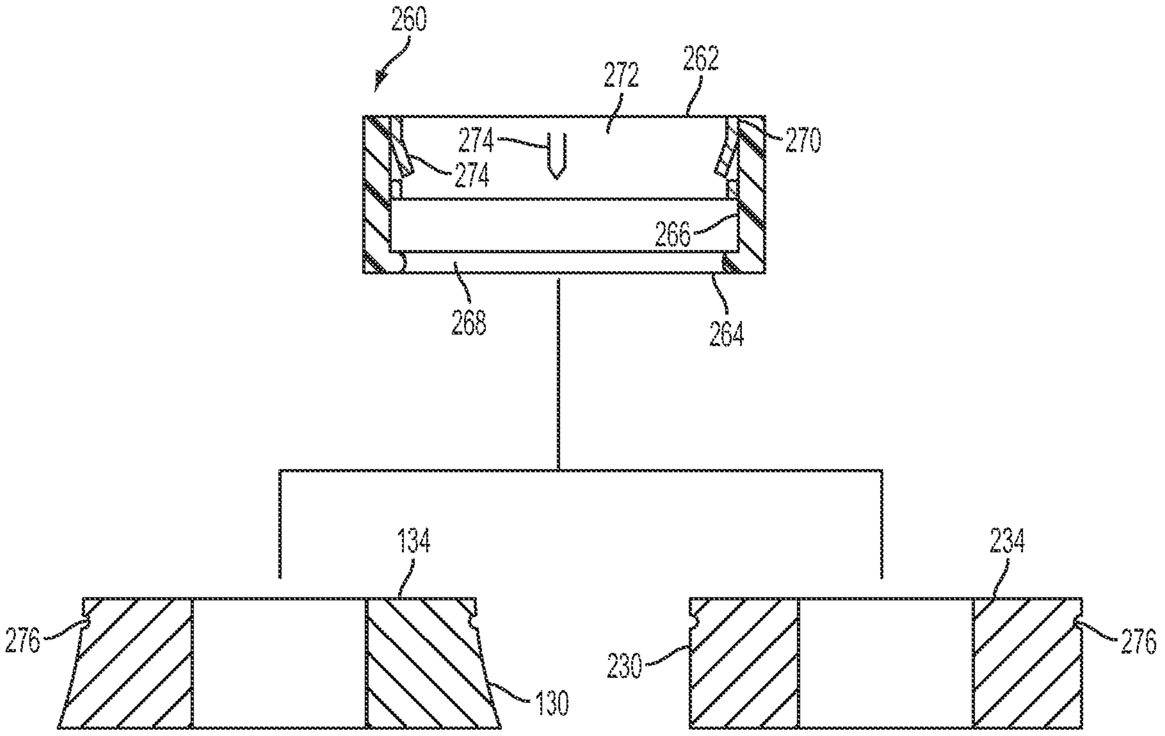
FIGS. 4D-4F are section views of another embodiment of a coupling arrangement that may removably attach the SMF to the AI.
Figure 4E:
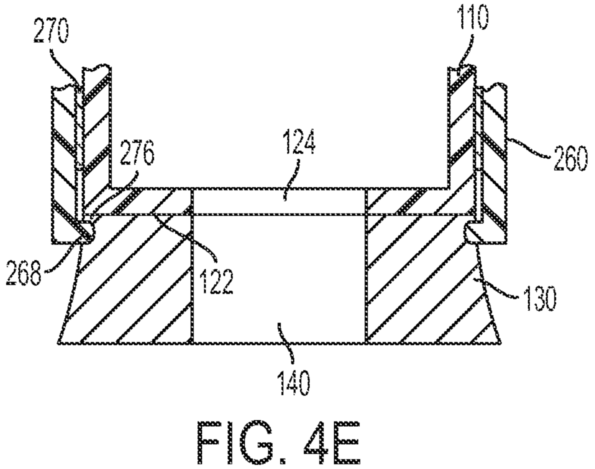
Figure 4F:
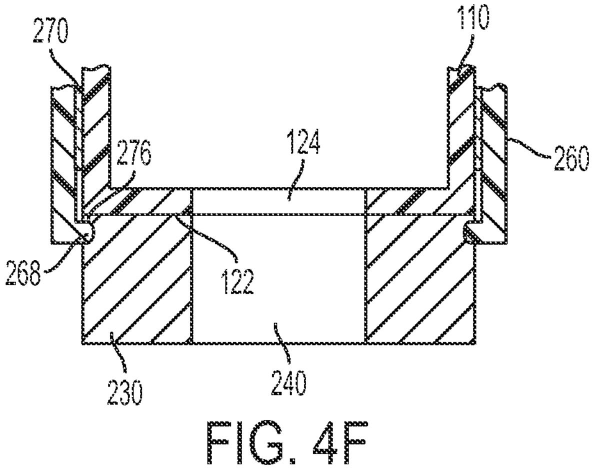

FIGS. 4D-4F illustrate another embodiment of a coupling arrangement that may removably attach the SMF 130, 230 to the AI 100. The coupling arrangement comprises an adaptor collar 260, which slides onto the injection end of the AI housing 110 and allows a snap-lock attachment of interchangeable SMFs 130, 230 to the AI 100. The adaptor collar 260 may include a metal sleeve 270 for affixing the adaptor collar 260 to the AI housing 110. The metal sleeve may comprise two or more spaced apart barb-like gripping elements 274 formed on an inner surface 272 of the metal sleeve 270. The metal sleeve 270 may be installed in the adaptor collar 260 on an inner surface 266 thereof adjacent to a first open end 262 of the collar 260. The metal sleeve 270 is sized to friction-fit against the inner surface 266 of the adaptor collar 260 so that it will not pull out of the collar 260 when unsnapping an SMF 130, 230 from the collar 260 or snapping an SMF 130, 230 onto the collar 260. When the adaptor collar 260 is pressed onto the injection end of the AI housing 110, the barb-like gripping elements 274 of the metal sleeve 270 may dig into and grip the AI housing 110 thereby preventing the removal of the adaptor collar 260 from the AI, particularly when unsnapping an SMF 130, 230 from the collar 260. A first member 268 of a snap locking arrangement may be formed on the inner surface 266 of the adaptor collar 260 adjacent to a second open end 264 thereof and a second member 276 of the snap locking arrangement may be formed on the side surface 138, 238 of the SMF 130, 230 adjacent to the first end surface 134, 234 thereof. One of the first and second members 268, 276 of the snap fastening arrangement may comprise a continuous or segmented bead (e.g., first member 268 illustrated in FIGS. 4D-4F) and the other one of the first and second members 268, 276 may comprise a continuous or segmented groove (e.g., second member 276 illustrated in FIGS. 4D-4F) adapted to removably receive the bead in a snap-fit manner. The snap locking arrangement allows users with hand-strength/dexterity issues to easily attach and remove a desired SMF 130, 230.

Figure 5A:
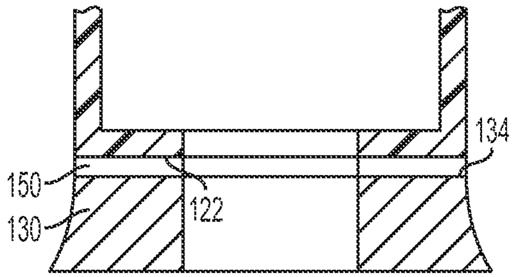
FIG. 5A is a section view illustrating another embodiment of a flexible skin manipulating flange attached to a surface of an autoinjector's housing with a layer or film of adhesive.
Figure 5B:
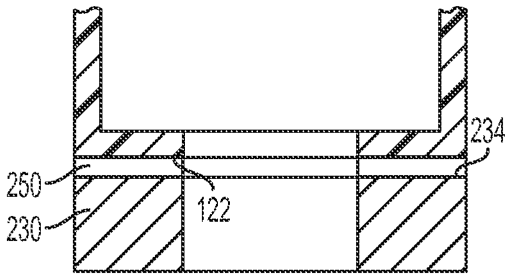
FIG. 5B is a section view illustrating a further embodiment of a flexible skin manipulating flange attached to the surface of an autoinjector's housing with a layer or film of adhesive.
Figure 6A:
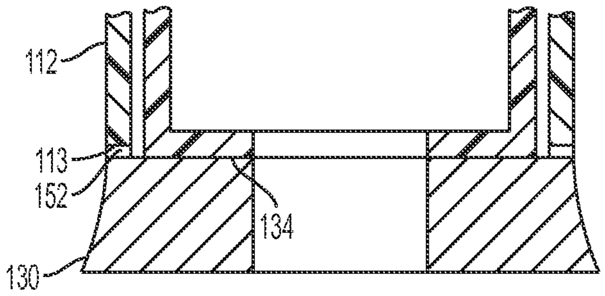
FIG. 6A is a section view illustrating a further embodiment of a flexible skin manipulating flange attached to an edge surface of an autoinjector's needle shield with a layer or film of adhesive.
Figure 6B:
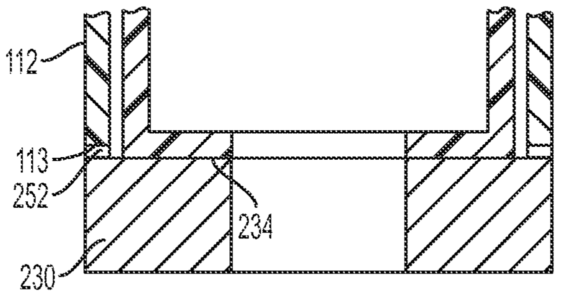
FIG. 6B is a section view illustrating a further embodiment of a flexible skin manipulating flange attached to an edge surface of an autoinjector's needle shield with a layer or film of adhesive.

In further embodiments, the SMF 130, 230 may be integrated into or permanently attached to the AI 100 during manufacturing. In some of these embodiments, integration or permanent attachment of the SMF 130, 230 may be facilitated by bonding the first end surface 134, 234 of the SMF 130, 230 to the front end wall 122 of the AI housing 110 with a layer or film 150, 250 of adhesive, as illustrated in FIGS. 5A and 5B. In other embodiments, integration or permanent attachment may be facilitated by bonding the first end surface 134, 234 of the SMF 130, 230 to the bottom edge surface 113 of the needle shield 112 with a layer or film 152, 252 of adhesive, as illustrated in FIGS. 6A and 6B.

Figure 7A:
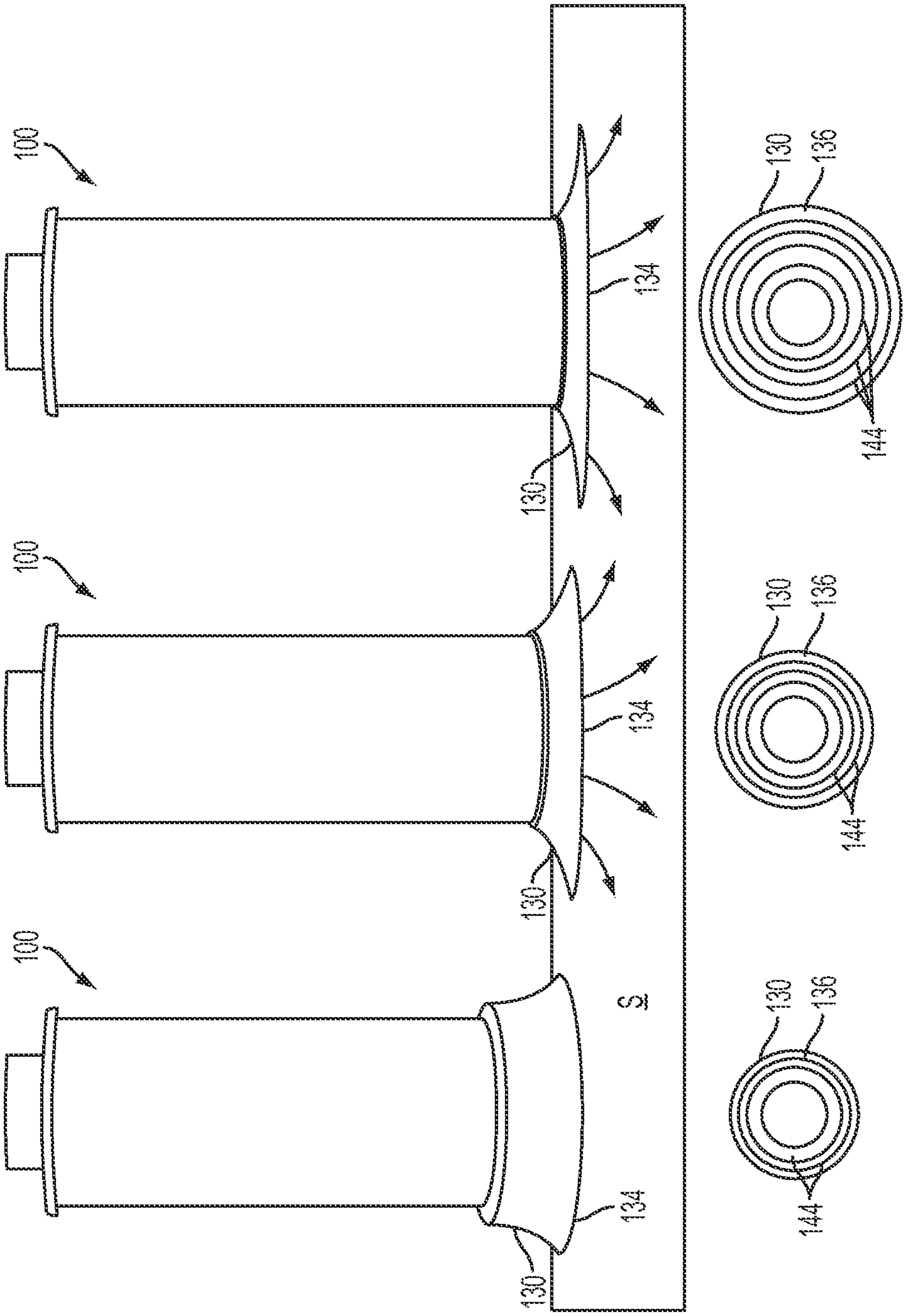
FIG. 7A is an elevation view illustrating the operation of a flexible skin manipulating flange having one or more ring-shape protrusions or ridges provided on the working surface of the flange, which aid in spreading or stretching the skin S at the injection site.
Figure 7B:
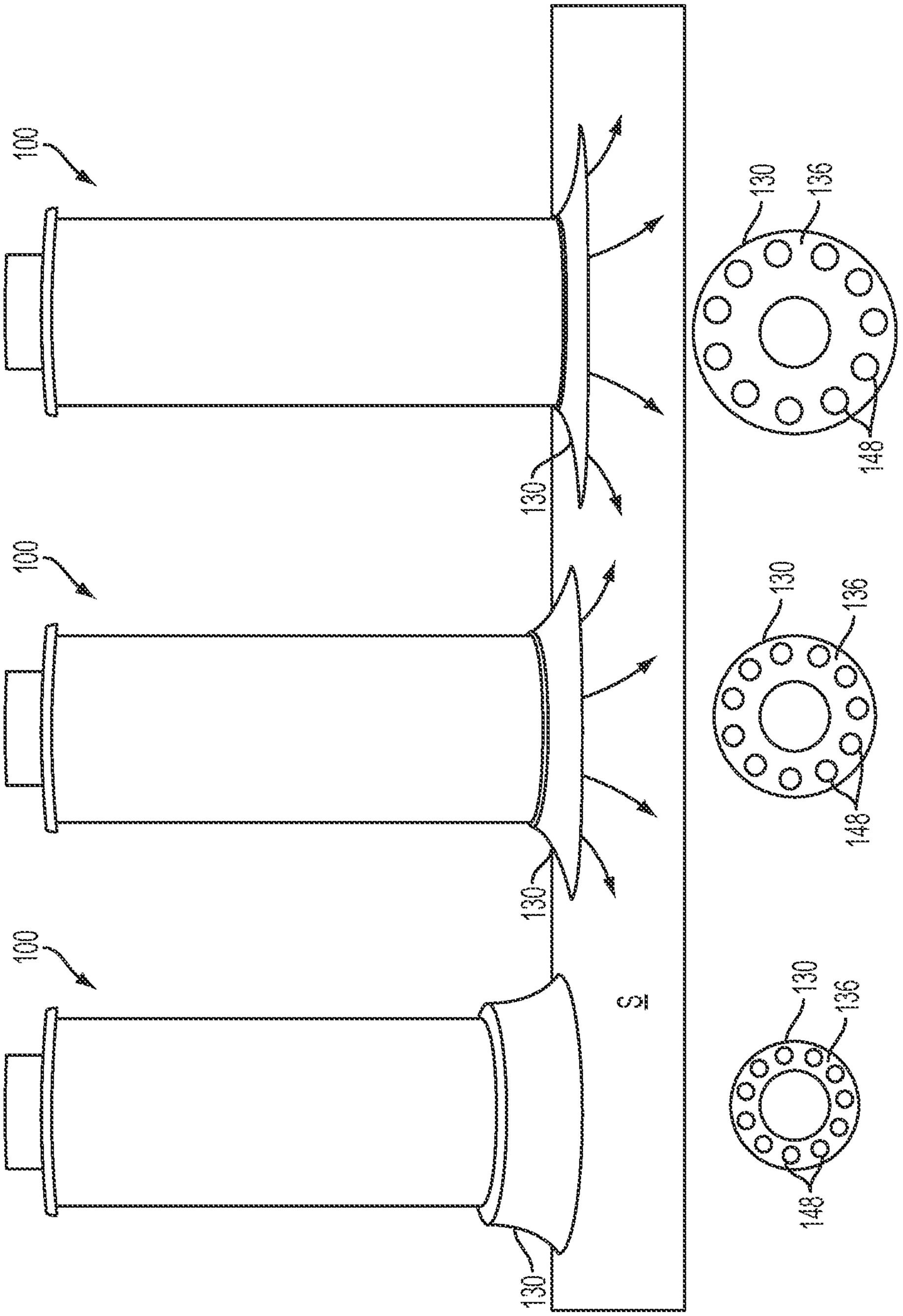
FIG. 7B is an elevation view illustrating the operation of a flexible skin manipulating flange having a circle of spaced apart protuberances or nubs provided on the working surface of the flange, which aid in spreading or stretching the skin S at the injection site.
Figure 7C:
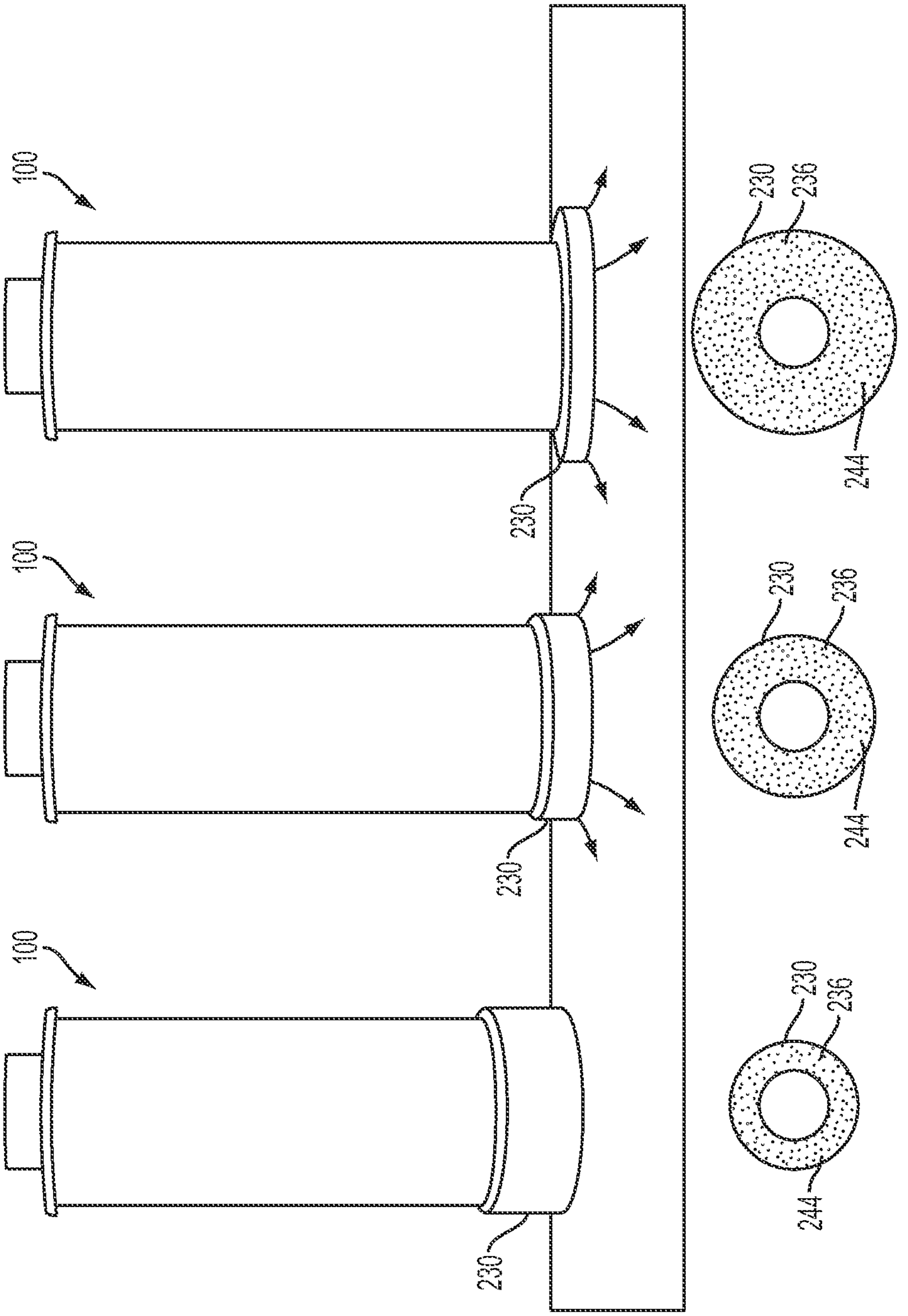
FIG. 7C is an elevation view illustrating the operation of a flexible skin manipulating flange having a sticky or grippy texture provided on the working surface of the flange, which aid in spreading or stretching the skin S at the injection site.

Referring now to FIGS. 7A-7C, the second end surface 134, 234 of the SMF 130, 230 can be provided with features, which aid in spreading or stretching the skin S at the injection site taut under the SMF 130, 230, as the SMF 130, 230 is pressed down to radially expand the SMF 130, 230. For example, in some embodiments, the second surface 134 of the SMP 130 (FIGS. 2A and 2B) may be provided with one or more ring-shape protrusions or ridges 244, as illustrated in FIG. 7A, or with a circle of spaced apart protuberances or nubs 148, as illustrated in FIG. 7B, which are selectively positioned to hold, stretch, and stabilize the skin S under the SMF 130, as the SMF 130 compresses, flattens, and radially expands in response to the AI 100 being pressed down into the skin S at the injection site. When the AI 100 is lifted off of the skin S, the SMF 130 returns to its original uncompressed and unflattened shape, thereby releasing the skin S.

If pinching of the skin S is desired, the ring-shape protrusions or ridges of the SMF 130 illustrated in FIG. 7A can also be used to raise the skin S into the SMF 130 to simulate pinching the skin, by lifting up slightly on the AI 100 after compressing and flattening the SMF 130.

In some embodiments, the second end surface 236 of the SMF 230 (FIGS. 3A and 3B) may be provided with a sticky or grippy texture, as illustrated in FIG. 7C, which holds, stretches and stabilizes the skin under the SMF, as the SMF compresses, flattens, and radially expands in response to the AI 100 being pressed down into the skin at the injection site. When the AI 100 is lifted off of the skin, the SMF returns to its original shape and releases the skin. If pinching of the skin S is desired, the stick or grippy texture provided on the second end surface 236 of the SMF 230 can also be used to raise the skin S to simulate pinching the skin by lifting up slightly on the AI 100 after compressing and flattening the SMF 230.

Figure 8A:
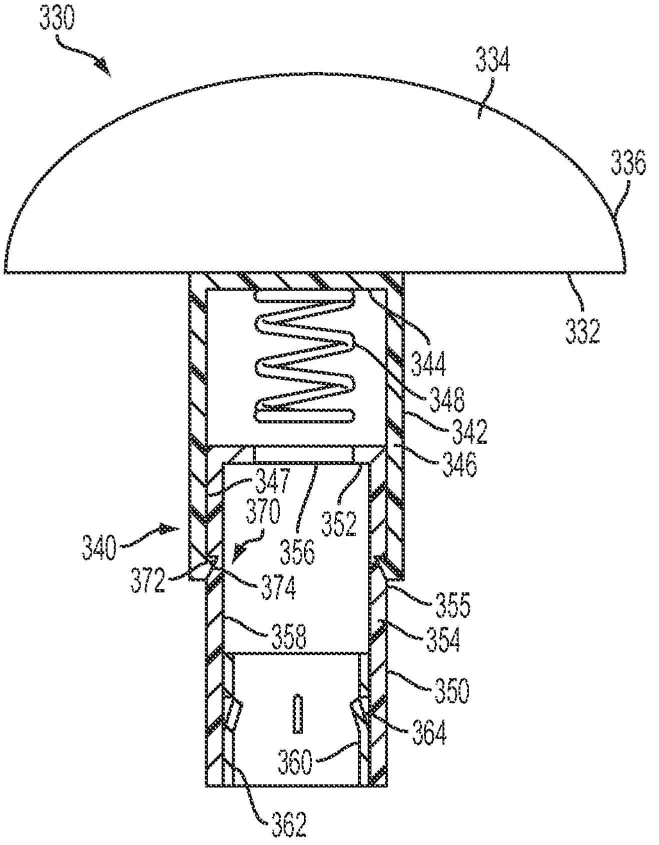
FIG. 8A is an elevation view illustrating an embodiment of a palm button device (illustrated in partial section) for an autoinjector.

FIG. 8A illustrates an embodiment of a palm button 330 device for easy arming and needle injection initiation of an AI. The palm button device 330 generally comprises a palm button 331 and a mounting arrangement 340 for affixing the palm button device 330 to an AI. The palm button device 330 provides better AI stability and easy activation with palm operation than with finger operation, and allows one handed operation of the AI. Further, the palm button device 330 makes it easier to train a user to handle and use the AI.

Figure 8B:
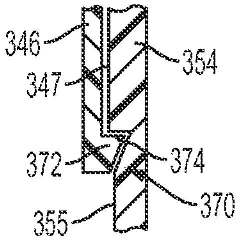
FIG. 8B is an enlarged section view illustrating an embodiment of a detent arrangement for coupling a base and an adaptor of the palm button device of FIG. 8A.
Figure 8C:
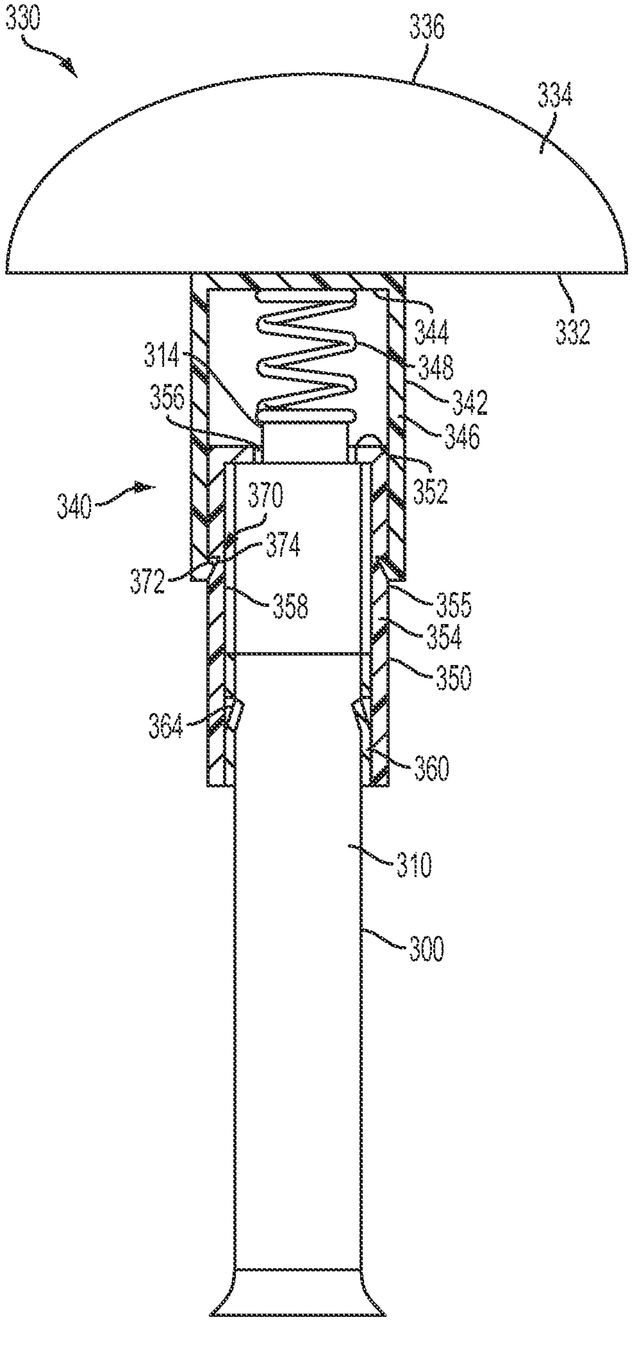
FIG. 8C is an elevation view illustrating the palm button of FIG. 8A affixed to an embodiment of an autoinjector.

Referring now to FIGS. 8A-8C, the palm button 331 of the device 330 may have a flat bottom surface 332 and a curved top surface 334. The curved top surface 334 may be sized to accommodate the inner surface or palm of the user's hand so that the palm button 331 naturally conforms to the majority of hand profiles. In some embodiments, the palm button 331 may be 6.0 cm long, 4.5 cm wide, and 3.5 cm tall. In other embodiments the palm button 331 may have other dimensions. The curved top surface 334 provides an ergonomic actuation surface for the palm button 331 so that the user can arm and initiate the needle injection cycle of an AI with a palm-push motion. In some embodiments, the curved top surface 334 of the palm button 331 may have a mushroom-shape or hemispherical-shape, to maximize gripping and easy pressing of the palm button 331.

The mounting arrangement 340 may comprise a base 342 extending from a generally central portion of the bottom surface 332 of the palm button 331 and an adaptor 350 movably or telescopically disposed within the base 342. The mounting arrangement 340 mechanically and operatively couples the palm button device 330 to an AI 300 (FIG. 8C). More specifically, the base 342 of the mounting arrangement 340 operatively couples the palm button 330 of the device 330 to the activation button 314 of the AI 300 and mechanically couples the palm button 330 to the adaptor 350. The adapter 350, in turn, is constructed to be pressed onto the activation end opposite to the injection end of the AI housing 310, to mechanically couple the palm button device 330 to the AI 300. The base 342 of the mounting arrangement 340 may comprise a top wall 344 and a cylindrical side wall 346 that depends from the periphery of the top wall 344. A biasing element 348, such as a coil spring, may extend down from the top wall 344 of the base 342. The adaptor 350 of the mounting arrangement 340 may comprise a top wall 352 and a cylindrical side wall 354 that depends from the periphery of the top wall 352. The top wall 352 may include an opening 356 to allow the activation button 314 of the AI 300 to extend therethrough. The adaptor 350 may further include a metal sleeve 360 comprising two or more spaced apart barb-like gripping elements 36 projecting from an inner surface 362 of the metal sleeve 360. The metal sleeve 360 may be disposed on an inner surface 358 of the adaptor side wall 354 in a friction-fit manner so that the metal sleeve 360 will not pull out of the adaptor 350 when operating the AI 300. When the adaptor 350 is slidably placed onto the activation end of the AI housing 310, the barb-like gripping elements 364 of the metal sleeve 360 may dig into and grip the AI housing 310, thereby preventing the removal of the palm button device 330 from the AI 300. When the user presses the palm button 331 down to arm and initiate the injection cycle of the AI 330, the biasing element 348 presses the activation button 314 of the AI 300 down and becomes compressed between the top wall 344 of the base 342 and the activation button of the AI 300. When the user releases the palm button 331, the compressed biasing element 348 returns the palm button 331 to the undepressed position and allows the activation button 314 of the AI 330 to return the undepressed position.

As best illustrated in FIG. 8B, a detent arrangement 370 may be provided for preventing the base 342 from being removed from the adaptor 350 when the palm button 331 is in an undepressed state, and for allowing the base 342 to move down relative to the adaptor 350 when the palm button 331 is depressed. A first member 372 of the detent arrangement may be formed on an inner surface 347 of the base 342 and a second member 374 of the detent arrangement may be formed on an outer surface 355 of the adaptor 350. One of the first and second members 372, 374 of the detent arrangement may comprise a continuous or segmented, downward facing, wedge-shaped projection (e.g., first member 372 illustrated in FIGS. 8A-8C) and the other one of the first and second members 372, 374 may comprise a continuous or segmented, downward facing wedge-shaped recess (e.g., second member 374 illustrated in FIGS. 8A-8C), which is adapted to receive the wedge-shaped projection 372.

The palm button device 330 may be made of a plastic material or any other suitable material including metal, hard rubber, and fiberglass. A soft, grippy coating 336 may be disposed over the top surface 334 of the palm button 331 to provide the palm button 331 with a softer feel and grip. Coating 336 may be a polyurethane gel elastomer layer or silicone-polyurethane copolymer layer.

Figure 8D:
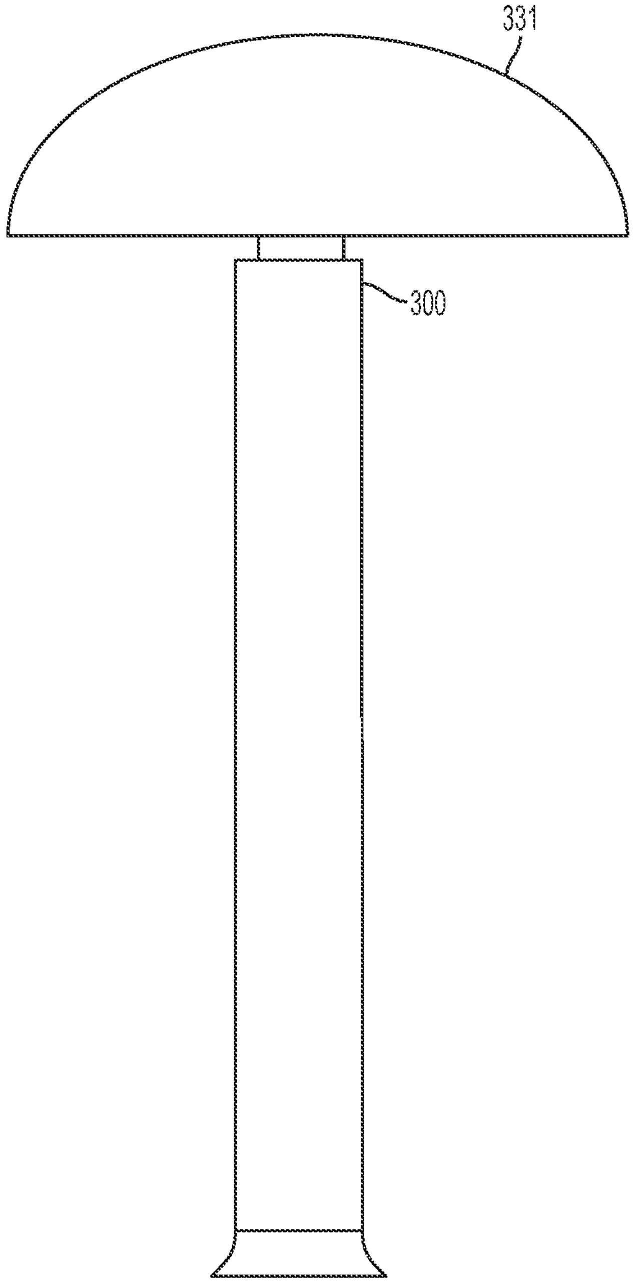
FIG. 8D is an exterior elevation view of the affixed palm button and autoinjector of FIG. 8C.

In some embodiments, the palm button 331 of the palm button device 330 may be integrated into the AI during manufacturing instead of being adapted for installation onto existing AIs. For example, in some embodiments, the palm button 330 may be adapted to replace the conventional activation button of the AI, as illustrated in FIG. 8D.

Figure 9A:
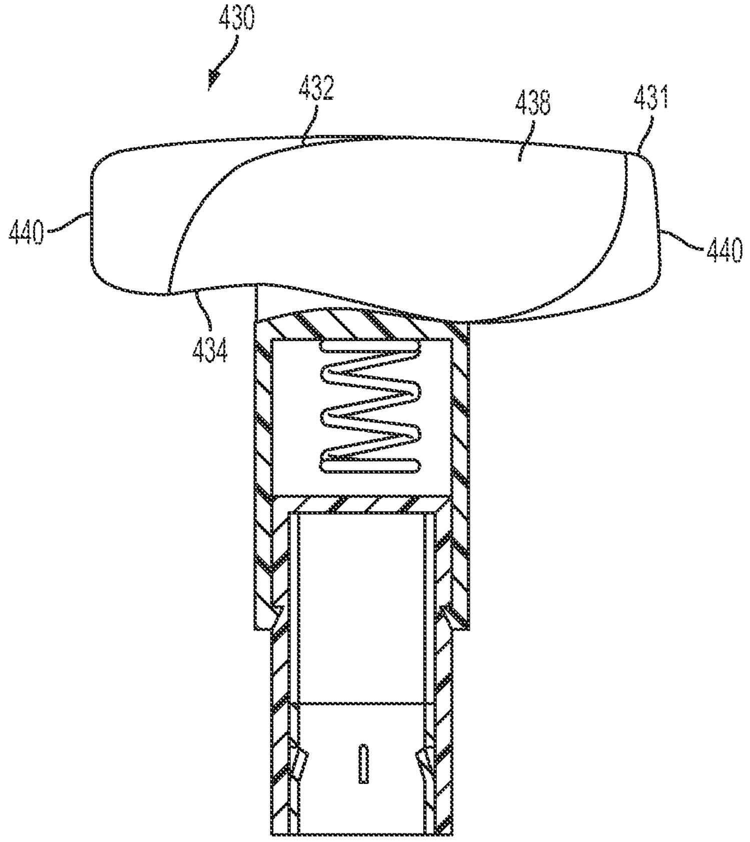
FIG. 9A is an elevation view illustrating another embodiment of the palm button device (illustrated in partial section).
Figure 9B:
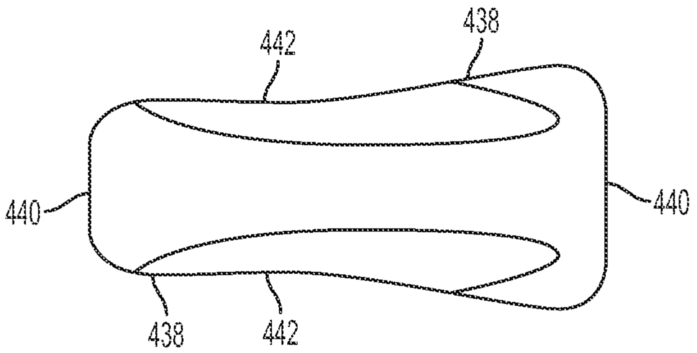
FIG. 9B is a top plan view of the palm button of the palm button device of FIG. 9A.

FIGS. 9A and 9B illustrate another embodiment of the palm button device 430 where like elements are identified by like reference numerals. The palm button device 430 is similar to the palm button device 330 illustrated in FIGS. 8A-8C except for the structure of palm button 431, which has an elongated shape formed by top and bottom walls 432 and 434, respectively, which are connected by side walls 438, and end walls 440. Accordingly, the palm button 431 and the mounting arrangement 340 define a T-shaped handle structure. A polyurethane gel elastomer layer 436 may be disposed over the top wall 432 of the palm button 431 to provide the palm button 431 with a softer feel and grip. In some embodiments, the palm button 431 may be 10.0 cm long, 4.0 cm wide, and 2.0 cm tall, although other embodiments of the palm button 431 may have other dimensions. In some embodiments, the palm button 431 may have indented side areas 442 (best illustrated in FIG. 9B) for receiving the user's thumb so that the user can more easily grasp or grip the palm button 431. In addition, the palm button 431 may be configured for both left- and right-handed use.

Figure 10A:
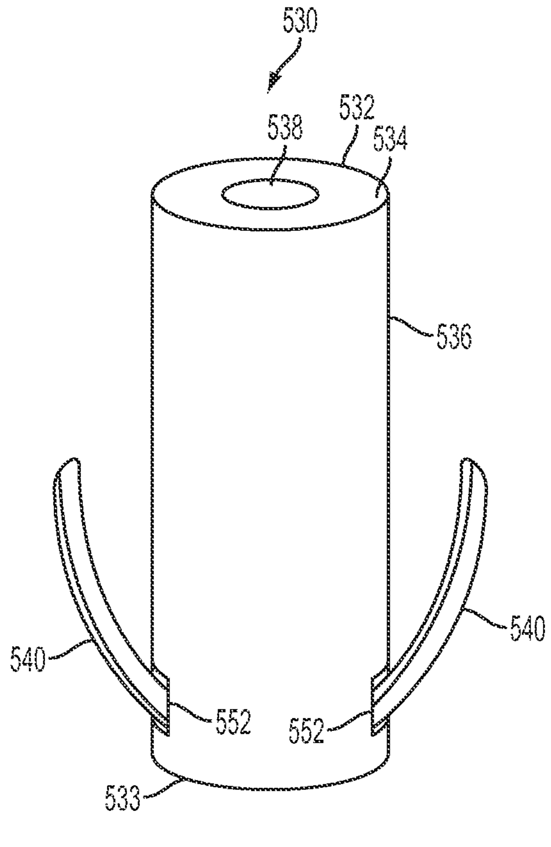
FIGS. 10A and 10B are elevation views of an embodiment of a hand holding device for one-handed operation of an autoinjector.
Figure 10B:
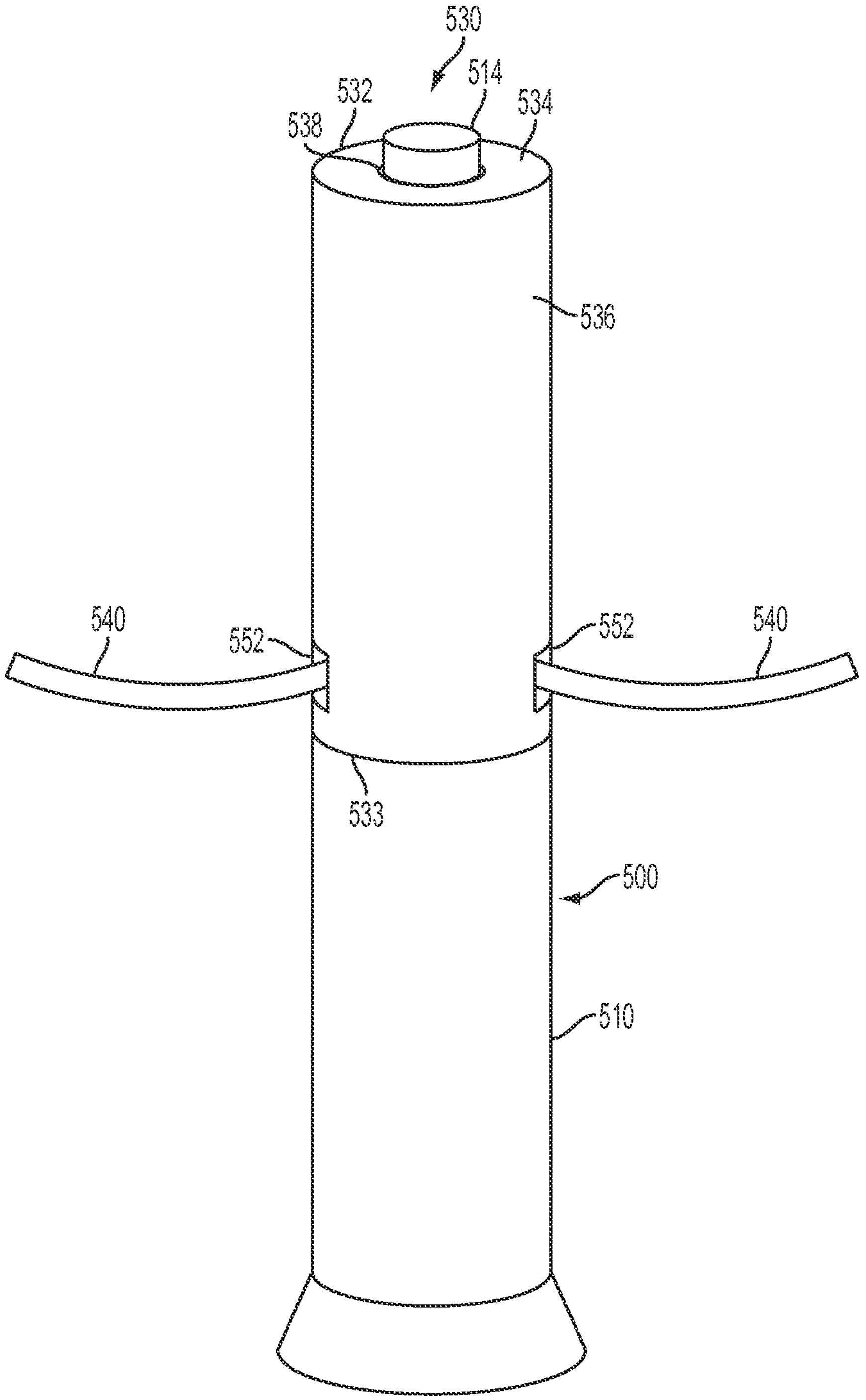
Figure 10C:
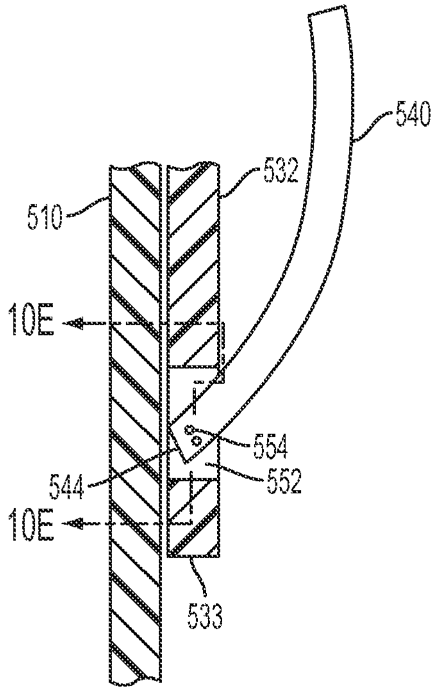
FIGS. 10C and 10D are n enlarged section views of an embodiment of the hand rest.
Figure 10D:
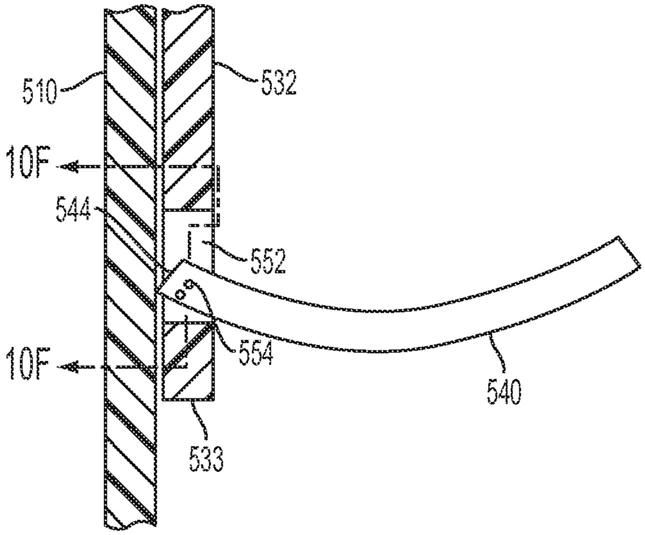

FIGS. 10A and 10B illustrate an embodiment of a hand holder (HH) device 530 for use with an AI 500. The HH device 530 provides an ergonomic shape for improved usability given the various physical limitations of a user's diseased state. The HH device 530 may comprise a sleeve 532 which functions as a hand grip, and one or more hand rests 540 pivotally connected to the sleeve 532 (two opposing hand rests 540 are illustrated in FIGS. 10A and 10B).

The sleeve 532 may comprise a top wall 534 and a cylindrical side wall 536 that depends from the periphery of the top wall 534. The wall 534 may include an aperture 538 for allowing the activation button 514 of the AI 500 to extend therethrough. The top wall 534 of the sleeve 532 can operate as stop to correctly position the sleeve 532 on the AI 500 during installation thereof. Once installed, the sleeve 532 of the HH device 530 forces the user to grip the AI 500 at the proper location so that the user can use the same hand to comfortably hold, stabilize and press the activation button 514 of the AI 500.

Figure 10E:
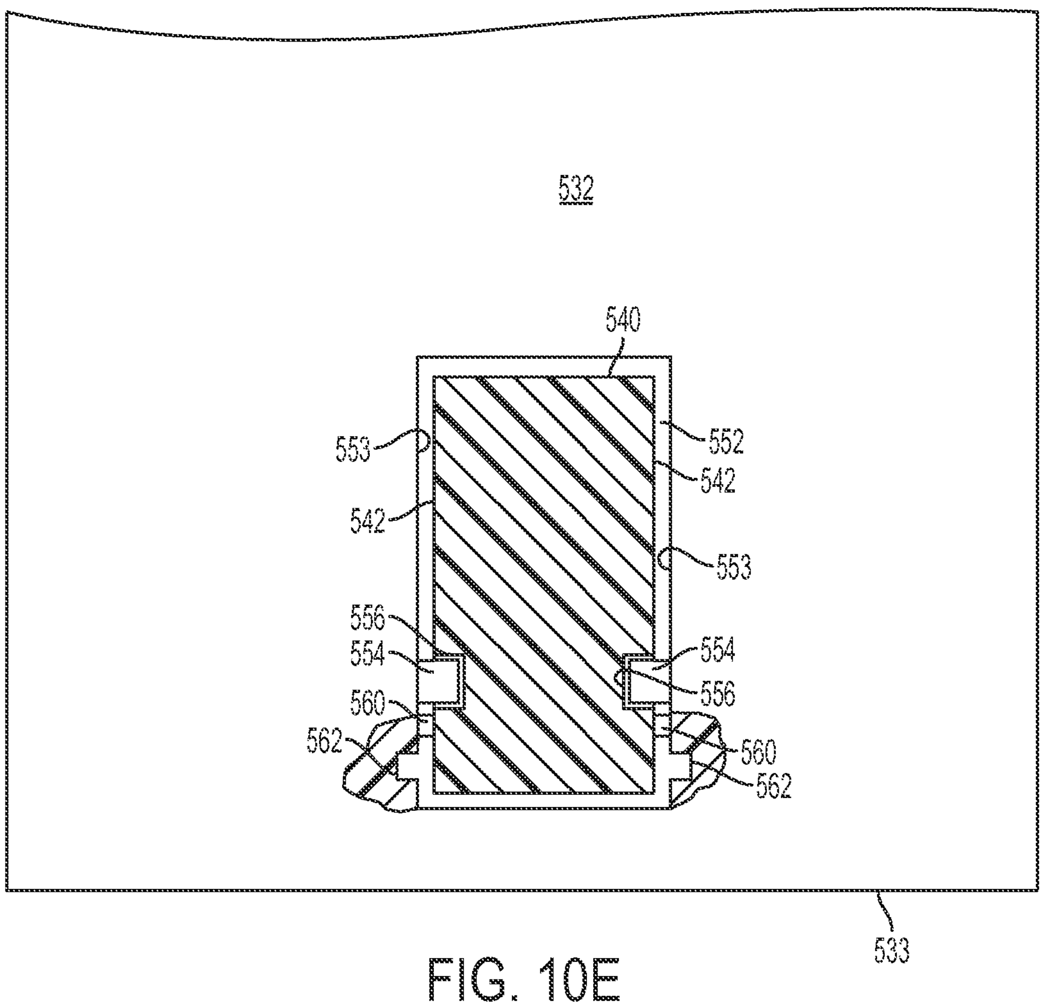
FIG. 10E is a section view through line 10E-10E of FIG. 10C.
Figure 10F:
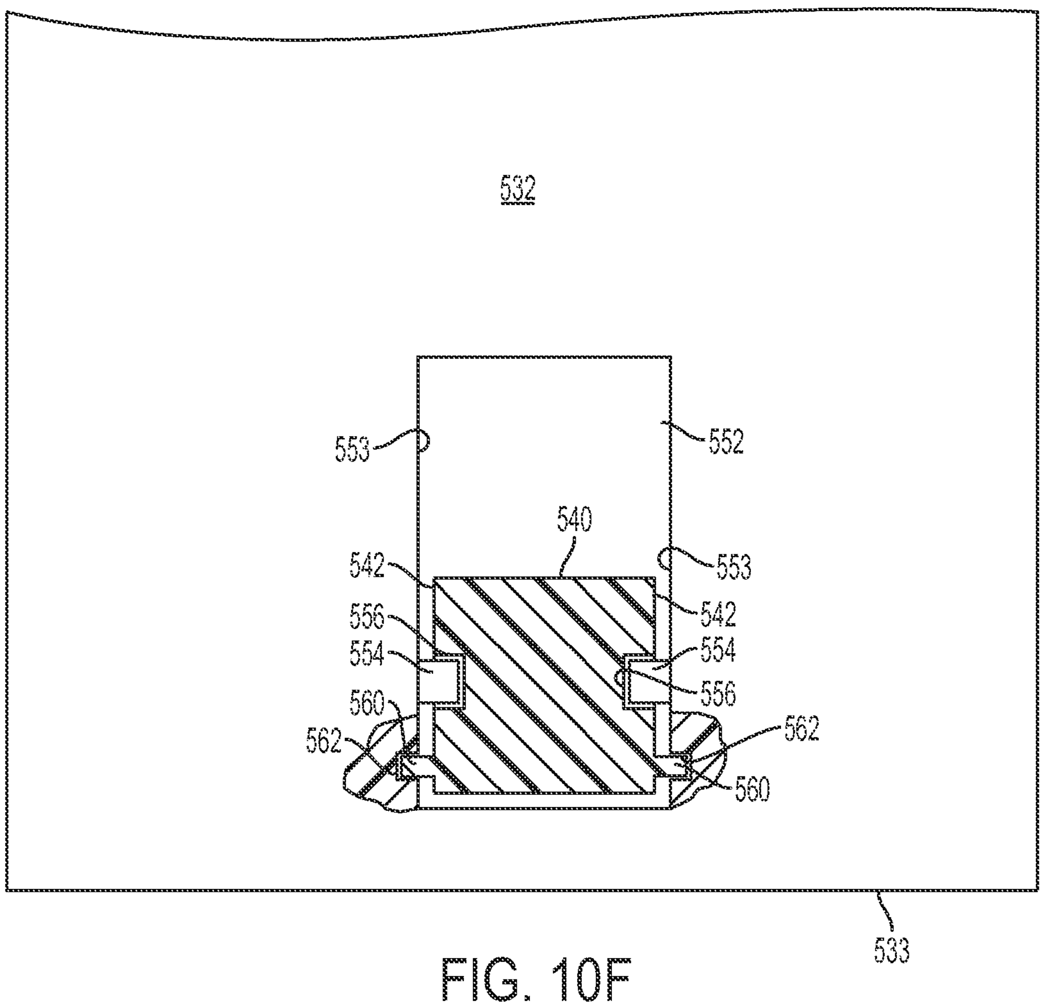
FIG. 10F is a section view through line 10F-10F of FIG. 10D.

Referring now to FIGS. 10C-10F, the hand rests 540 of the HH device 530 may be constructed as arm-like members. The hand rest arms 540 may be pivotally attached to the sleeve 532 by pivot pin structures. As best illustrated in FIGS. 10E and 10F, each pivot pin structure may include a slot 552 formed in the sleeve 532, a pair of axially aligned pivot pins 554, and a pair of axially aligned pivot pin receiving apertures 556. The slots 552 may be formed just above the open end 533 of the sleeve 532. The pivot pins 554 may extend from lateral edges 553 of the slots 552 and the pivot pin receiving apertures 556 may be formed on side surfaces 542 of the hand rest arms 540, adjacent to the attachment ends 544 of the hand rest arms 540. The pivot pin structure allows the hand rest arm 540 to be pivoted between an up position (FIG. 10A) and a down position (FIG. 10B). In the down position, the hand rest arms 540 extend out from and are generally perpendicular to the sleeve 532 and, therefore, operate to hold the user's hand on the AI 500 in the proper position by preventing the user's hand from sliding down the sleeve 532 and onto the AI 500. The hand rest arms 540 may be contoured to receive the hypothenar muscle area of the user's hand adjacent to the little finger (digiti minimi). The hand rest arms 540 may also function as clamps in the down position, to affix the HH device 500 to the AI 500. As best illustrated in FIGS. 10E and 10F, the hand rest arms 540 in such embodiments can each include a projection 546 at the attachment end 544 thereof (FIGS. 10C and 10D), which engages the housing 510 of the AI 500 when the hand rest arm 540 is in the down position, thus enabling the arm 540 to clamp and affix the HH device 500 to the AI 500. Further, each of the hand rest arms 540 may be provided with a detent arrangement for holding hand rest arms 540 in the down (clamping) position. The detent arrangement may comprise a projection 560 extending from each side surface 542 of the hand rest arm 540 and a recess 562 formed in each lateral edge surface 553 of the slot 552. When the hand rest arm 540 is in the up position, as illustrated in FIG. 10E, the projections 560 of the detent arrangement slidably engage the lateral edge surfaces 553 of the slot 552. When the hand rest arm 540 is pivoted down into the clamping position, as illustrated in FIG. 10F, the projections 560 slide along the lateral edge surfaces 553 of the slot 552 and enter the recesses 562 thereby locking the hand rest arm 540 in the down and clamping position. The detent arrangement can be unlocked by applying an upward force on the hand rest arm 540, which is sufficient to withdraw the projections 560 from the recesses 562, thereby allowing the arm 540 to be pivoted back to the up position.

In further embodiments, an adhesive or a metal sleeve comprising spaced apart barb-like gripping elements similar to the metal sleeve described above with respect to the palm button device can be provided on the inner surface of the sleeve 532 to affix the HH device 530 to the AI 500. The adhesive or metal sleeve can be used in addition to the hand rest arms 540 with the earlier described clamping structures or alone with hand rest arms 540 that do not have the clamping structures.

When the hand rest arms 540 are in the up position, as illustrated in FIG. 10A, the HH device 530 can be easily packaged. Once removed from its package, the HH device 530 can be installed on the AI 500. During installation, the HH device 530 may be slidably placed over the end of the AI 500 until the activation button 514 extends through the aperture 538 in the top wall 534 of the sleeve 532 and the top wall 534 engages the end wall of the AI 500 which surrounds the activation button 514, thereby properly positioning the sleeve of the HH device on the AI. The hand rest arms 540 may then be pivoted down from the up position to the down position where the hand rest arms 540 may engage the AI 500 to affix the HH device 530 to the AI 500 and prevent downward slippage of the user's hand as described earlier.

Figure 10G:
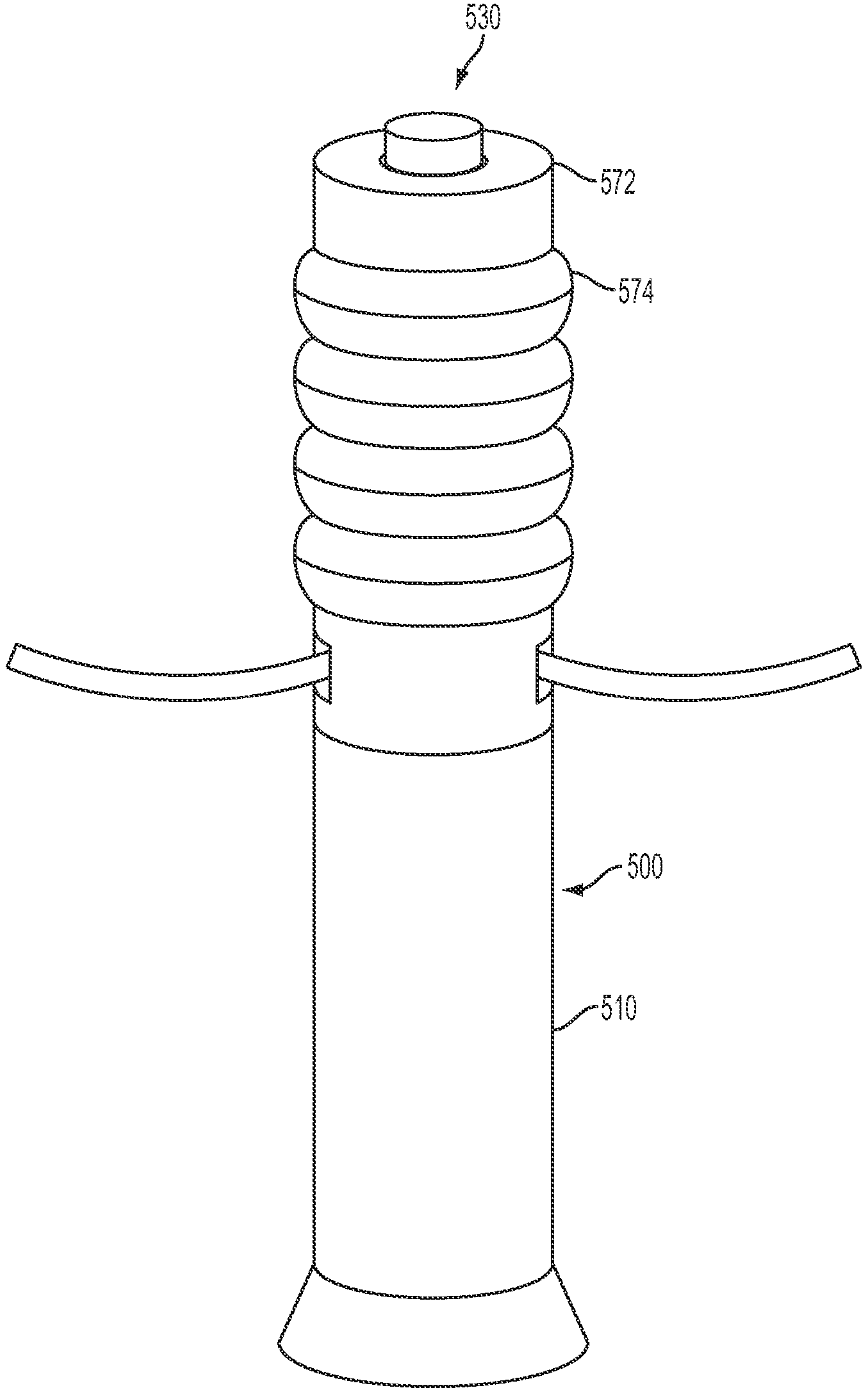
FIG. 10G is an elevation view of another embodiment of a hand holding device affixed to an embodiment of an autoinjector.

As illustrated in FIG. 10G, some embodiments of the HH device 530 may have a sleeve 572 with a contoured hand grip 574 that enhances the ergonomic holding feature of the HH device 530. The hand grip 574 may be unitary with the sleeve 572 or applied to the sleeve as a separate layer or oversleeve. Separate layer or oversleeve types of hand grips 574 may be made of a soft, polyurethane gel elastomer material, or any other material suitable for finger or hand gripping.

Figure 11A:
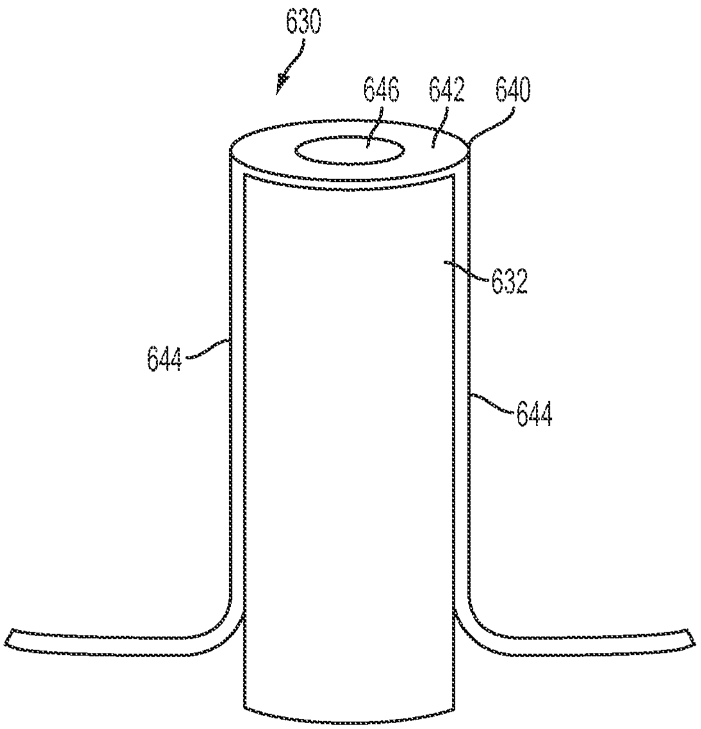
FIGS. 11A and 11B are elevation views of a further embodiment of a hand holding device for one-handed operation of an autoinjector.
Figure 11B:
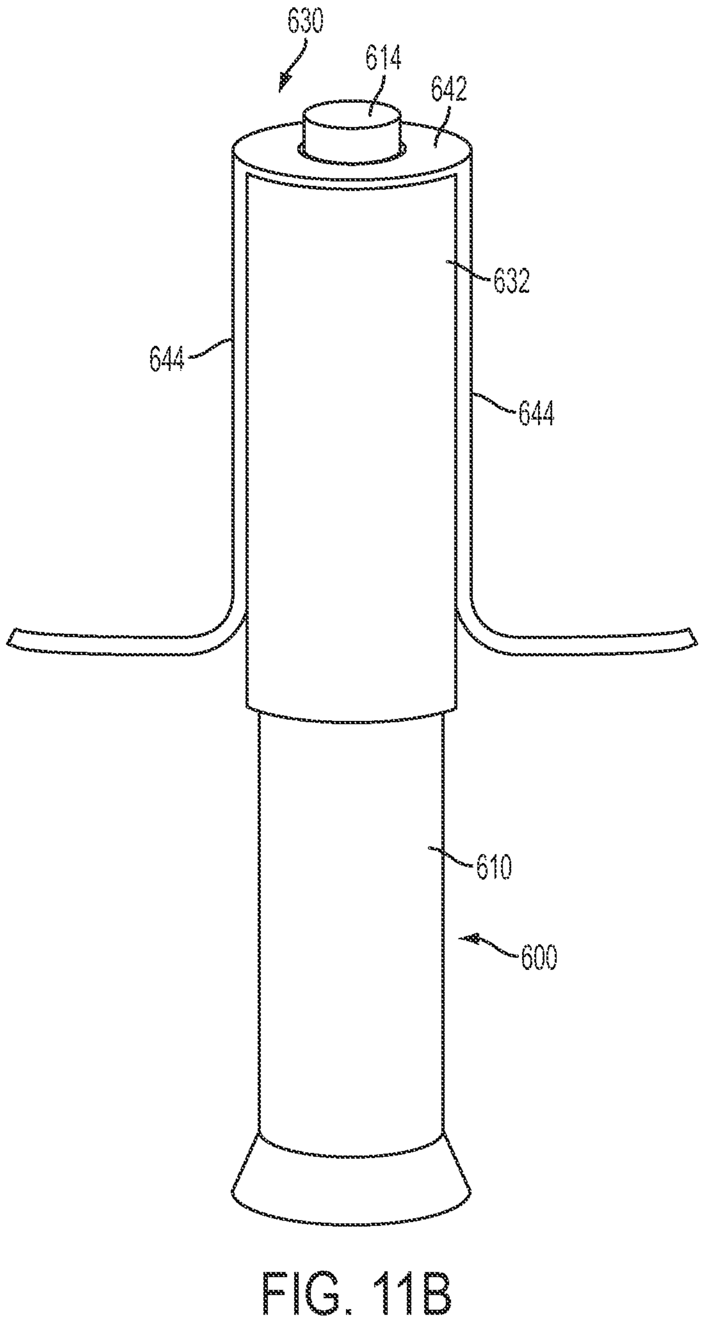

FIGS. 11A and 11B illustrate another embodiment of a hand holder (HH) device 630 for use with an AI 600. The HH device 630 may comprise an open-ended sleeve 632 and a fixed hand rest arrangement 640 disposed over one of the open ends of the sleeve 632. The fixed hand rest arrangement 640 may be a unitary member that includes a top wall 642 and two L-shaped hand rests 644 that depend from the periphery of the top wall 642. The bottom portion 645 of each hand rest extends out from the sleeve and may be contoured to receive the hypothenar muscle area of the user's hand adjacent to the little finger (digiti minimi). The top wall 642 may include an aperture 646 for allowing the activation button 614 of the AI 600 to extend therethrough. As in the previous embodiment, the top wall 642 can operate as stop to correctly position the sleeve 632 on the AI 600 during installation thereof. Once installed, the sleeve 632 of the HH device 630 forces the user to grip the AI 600 at the proper location so that the user can use the same hand to comfortably hold, stabilize and press the activation button 614 of the AI 600. The hand rest arms hold the user's hand on the AI 600 in the proper position by preventing the user's hand from sliding down the sleeve 632 and onto the AI 600. The inner surface of the sleeve 632 of the HH device 630 can be provided with a metal sleeve having spaced apart barb-like gripping elements similar to the metal sleeve described above with respect to the palm button device, to affix the HH device 630 to the housing 610 of the AI 600. An adhesive may also be used alone or with the metal sleeve or other mechanical means, to affix the HH device 630 to the housing 610 of the AI 600.

The HH device may be provided as an accessory item for the AI or integrated into the AI. In some embodiments, the HH device may function as an extension to the housing of the AI once affixed or attached to the AI, thereby functioning as a ergonomic holding feature, as described earlier. The HH device may be utilized on multiple types of AIs, including AIs that have only single activation feature (e.g., a needle shield), and AIs that have two activation features (e.g., a needle shield and an activation button). In some embodiments, the activation button may be located on the side of the AI instead of the top or rear wall of the AI.

In other embodiments, the HH device may be constructed and adapted as an active component of the AI, such that once affixed, attached, or placed on the AI, it can operate to activate the activation button of the AI in response to the application of a downward force on the HH device which causes the sleeve of the HH device to move axially relative to the housing of the AI and depress the AI's activation button. Such embodiments will allow the user to utilize the benefit of the AI's ergonomic design to provide additional leverage to depress the activation button (for AIs that have two feature activation (e.g., a needle shield and an activation button).

In still further embodiments, the HH device may be permanently attached to the AI during manufacturing. In such embodiments, the HH device may be constructed and adapted as a single or multiple use component.

Figure 12A:
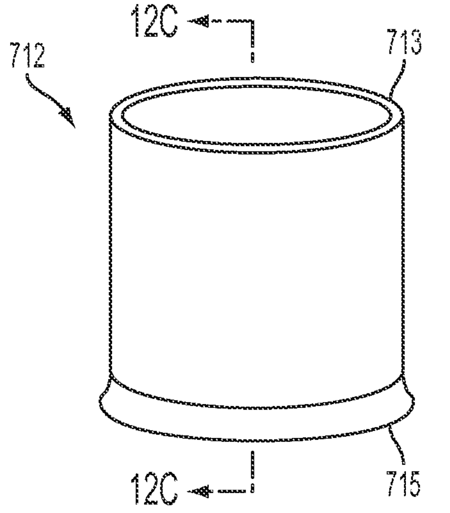
FIG. 12A is an elevation view illustrating an embodiment of an ergonomic needle shield for an autoinjector.
Figure 12B:
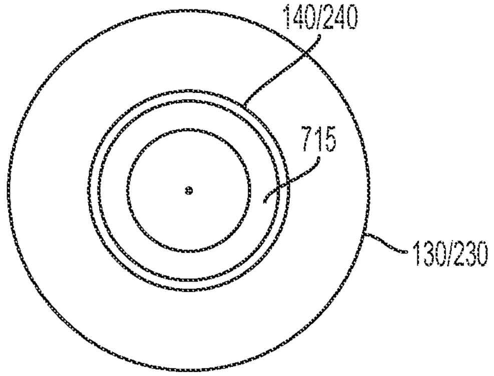
FIG. 12B is a bottom plan view of an embodiment of an autoinjector illustrating the ergonomic needle shield and a skin manipulating flange that has been adapted for use with the needle shield.
Figure 12C:
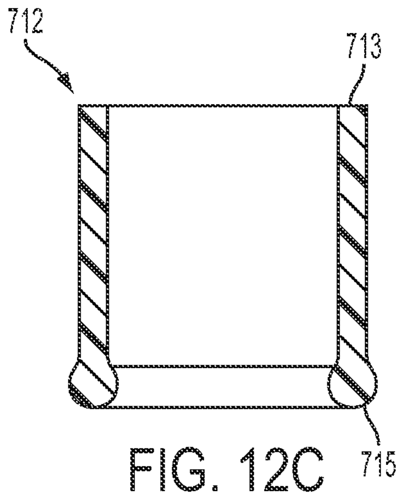
FIG. 12C is a section view through line 12C-12C of FIG. 12A.

FIGS. 12A-12C illustrate an embodiment of a needle shield 712 for use in an AI 700. The needle shield 712 may have a cylindrical shape and includes a first edge surface 713 and a second edge surface 715 opposite to the first edge surface 713. The needle shield 712 may be constructed so that the second edge surface 715 contacts the skin at the injection site during the operation of the AI. As illustrated in FIGS. 12A and 12C, the second edge surface of the needle shield may be configured as an enlarged, rounded lip, which makes contact with the user's skin more comfortable. The enlarged, rounded lip 715 has a larger surface area than the sharp edges of conventional needle shields, thus, making skin contact more comfortable during the injection process. As illustrated in FIG. 12B, the SMFs 130, 230 described earlier can be modified for use with AIs utilizing the needle shield of the present disclosure, by increasing the diameter of the needle aperture 140, 240 that extends through the SMF 130, 230, to accommodate the enlarged, round lip 715 of the needle shield.

In some embodiments, the needle shield 700 may be colored to indicate to the user that the injection is completed. More specifically, when the injection cycle has been completed and the colored needle shield 712 is subsequently deployed to cover the exposed injection needle, the deployed, colored needle shield 700 indicates to the user that the injection is completed.

The syringe or other primary container of the AI may be prefilled with a pharmaceutical product, such as an erythropoiesis stimulating agent (ESA), which may be in a liquid or a lyophilized form. An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins comprise erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins comprise, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (comprising EMP1/Hematide), and mimetic antibodies. Exemplary erythropoiesis stimulating proteins comprise erythropoietin, darbepoetin, erythropoietin agonist variants, and peptides or antibodies that bind and activate erythropoietin receptor.

The term erythropoiesis stimulating protein comprises without limitation Epogen® (epoetin alfa), Aranesp® (darbepoetin alfa), Dynepo® (epoetin delta), Mircera® (methyoxy polyethylene glycol-epoetin beta), Hematide™ (peginesatide), MRK-2578, INS-22, Retacrit® (epoetin zeta), Neorecormon® (epoetin beta), Silapo™ (epoetin zeta), Binocrit® (epoetin alfa), epoetin alfa Hexal, Abseamed™ (epoetin alfa), Ratioepo™ (epoetin theta), Eporatio™ (epoetin theta), Biopoin™ (epoetin theta), epoetin alfa, epoetin beta, epoetin zeta, epoetin theta, and epoetin delta.

The term erythropoiesis stimulating protein further comprises the molecules or variants or analogs as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,830,851; 5,856,298; 5,955,422; 5,986,047; 6,030,086; 6,310,078; 6,391,633; 6,583,272; 6,586,398; 6,900,292; 6,750,369; 7,030,226; 7,084,245; and 7,271,689; U.S. Publ. Nos. 2002/0155998; 2003/0077753; 2003/0082749; 2003/0143202; 2003/0215444; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0040858; 2006/0088906; and 2006/0111279; and PCT Publ. Nos. WO 91/05867; WO 95/05465; WO 96/40772; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667;

WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and WO 2007/136752.

Alternatively, the syringe or other primary container of the AI may also be prefilled with other products. Examples of other pharmaceutical products that may be used may comprise, but are not limited to, therapeutics such as a biological (e.g., Enbrel® (etanercept, TNF-receptor/Fc fusion protein, TNF blocker), anti-TNF antibodies such as adalimumab, infliximab, certolizumab pegol, and golimumab; anti-IL-12 antibodies such as ustekinumab, other Fc fusions such as CTL4A:Fc also known as abacept; Neulasta® (pegylated filgastrim, pegylated G-CSF, pegylated hu-met-G-CSF), Neupogen® (filgrastim, G-CSF, hu-met-G-CSF), Nplate® (romiplostim), Vectibix® (panitumumab), Sensipar® (cinacalcet), and Xgeva® and Prolia® (each denosamab, AMG 162); as well as other small molecule drugs, a therapeutic antibodies, a polypeptides, proteins or other chemicals, such as an iron (e.g., ferumoxytol, iron dextrans, ferric glyconate, and iron sucrose). The therapeutic may be in liquid form, or reconstituted from lyophilized form.

Among particular illustrative proteins that can be used in the syringe or other primary container of the AI are antibodies, peptibodies, pegylated proteins, polypeptides, and related proteins (comprising fusions, fragments, analogs, variants or derivatives thereof) for example, proteins that specifically bind to: OPGL; IL-4 receptor; interleukin 1-receptor 1 ("IL1-R1"); angiopoietin-2 (Ang2); NGF; CD22; IGF-1; B-7 related protein 1 (B7RP1); IL-15; IL-17 Receptor A: IFN gamma; TALL-1; parathyroid hormone ("PTH"); thrombopoietin receptor ("TPO-R"); hepatocyte growth factor ("HGF"); TRAIL-R2; Activin A; TGF-beta; amyloid-beta; □c-Kit; □□4□7: and IL-23 or one of its subunits; and other therapeutic proteins.

The syringe or other primary container of the AI may also be prefilled with OPGL specific antibodies, peptibodies, and related proteins, and the like (also referred to as RANKL specific antibodies, peptibodies and the like), comprising fully humanized and human OPGL specific antibodies, particularly fully humanized monoclonal antibodies, comprising but not limited to the antibodies described in PCT Publ. No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, comprising the OPGL specific antibodies having either the light chain of SEQ ID NO: 2 therein as set forth in FIG. 2 therein and/or the heavy chain of SEQ ID NO:4 therein, as set forth in FIG. 4 therein, each of which is individually and specifically incorporated by reference herein in its entirety fully as disclosed in the foregoing Publication.

The syringe or other primary container of the AI may also be prefilled with myostatin binding proteins, peptibodies, and related proteins, and the like, comprising myostatin specific peptibodies, particularly those described in US Publ. No. 2004/0181033 and PCT Publ. No. WO 2004/058988, which are incorporated by reference herein in their entirety particularly in parts pertinent to myostatin specific peptibodies, comprising but not limited to peptibodies of the mTN8-19 family, comprising those of SEQ ID NOS: 305-351, comprising TN8-19-1 through TN8-19-40, TN8-19 con1 and TN8-19 con2; peptibodies of the mL2 family of SEQ ID NOS: 357-383 therein; the mL15 family of SEQ ID NOS: 384-409; the mL17 family of SEQ ID NOS: 410-438 therein; the mL20 family of SEQ ID NOS: 439-446 therein; the mL21 family of SEQ ID NOS: 447-452 therein; the mL24 family of SEQ ID NOS: 453-454 therein; and those of SEQ ID NOS: 615-631 therein, each of which is individually and specifically incorporated by reference herein in their entirety fully as disclosed in the foregoing publication.

The syringe or other primary container of the AI may also be prefilled with IL-4 receptor specific antibodies, peptibodies, and related proteins, and the like, particularly those that inhibit activities mediated by binding of IL-4 and/or IL-13 to the receptor, comprising those described in PCT Publ. No. WO 2005/047331 or PCT Appl. No. PCT/US2004/03742 and in US Publ. No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication.

The syringe or other primary container of the AI may also be prefilled with IL1-R1 specific antibodies, peptibodies, and related proteins, and the like, comprising but not limited to those described in U.S. Publ. No. 2004/097712A1, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. publication.

The syringe or other primary container of the AI may also be prefilled with Ang2 specific antibodies, peptibodies, and related proteins, and the like, comprising but not limited to those described in PCT Publ. No. WO 03/057134 and U.S. Publ No. 2003/0229023, each of which is incorporated herein by reference in its entirety particularly in parts pertinent to Ang2 specific antibodies and peptibodies and the like, especially those of sequences described therein and comprising but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also comprising anti-Ang 2 antibodies and formulations such as those described in PCT Publ. No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication.

The syringe or other primary container of the AI may also be prefilled with NGF specific antibodies, peptibodies, and related proteins, and the like comprising, in particular, but not limited to those described in US Publ. No. 2005/0074821 and U.S. Pat. No. 6,919,426, which are incorporated herein by reference in their entirety particularly as to NGF-specific antibodies and related proteins in this regard, comprising in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication.

The syringe or other primary container of the AI may also be prefilled with CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, comprising but not limited to humanized and fully human monoclonal antibodies, particularly comprising but not limited to human CD22 specific IgG antibodies, such as, for instance, a dimer of a human-mouse monoclonal hLL2 gamma-chain disulfide linked to a human-mouse monoclonal hLL2 kappa-chain, comprising, but limited to, for example, the human CD22 specific fully humanized antibody in Epratuzumab, CAS registry number 501423-23-0;

The syringe or other primary container of the AI may also be prefilled with IGF-1 receptor specific antibodies, peptibodies, and related proteins, and the like, such as those described in PCT Publ. No. WO 06/069202, which is incorporated herein by reference in its entirety as to IGF-1 receptor specific antibodies and related proteins, comprising but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing International Publication.

Also among non-limiting examples of anti-IGF-1R antibodies for use in the methods and compositions of the present invention are each and all of those described in: (i) US Publ. No. 2006/0040358 (published Feb. 23, 2006), 2005/0008642 (published Jan. 13, 2005), 2004/0228859 (published Nov. 18, 2004), comprising but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein; (ii) PCT Publ. No. WO 06/138729 (published Dec. 28, 2006) and WO 05/016970 (published Feb. 24, 2005), and Lu et al., 2004, J Biol. Chem. 279:2856-65, comprising but not limited to antibodies 2F8, A12, and IMC-A12 as described therein; (iii) PCT Publ. No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003); (iv) US Publ. No. 2005/0084906 (published Apr. 21, 2005), comprising but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein; (v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, comprising but not limited to antibody EM164, resurfaced EM164, humanized EM164, huEM164 v1.0, huEM164 v1.1, huEM164 v1.2, and huEM164 v1.3 as described therein; (vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, comprising but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein; (vii) US Publ. Nos. 2005/0136063 (published Jun. 23, 2005) and 2004/0018191 (published Jan. 29, 2004), comprising but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), comprising but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors.

The syringe or other primary container of the AI may also be prefilled with B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011941, which are incorporated herein by reference in their entireties as to such antibodies and related proteins, comprising but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Publication.

The syringe or other primary container of the AI may also be prefilled with IL-15 specific antibodies, peptibodies, and related proteins, and the like, such as, in particular, humanized monoclonal antibodies, particularly antibodies such as those disclosed in U.S. Publ. Nos. 2003/0138421; 2003/

023586; and 2004/0071702; and U.S. Pat. No. 7,153,507, each of which is incorporated herein by reference in its entirety as to IL-15 specific antibodies and related proteins, comprising peptibodies, comprising particularly, for instance, but not limited to, HuMax IL-15 antibodies and related proteins, such as, for instance, 146B7.

The syringe or other primary container of the AI may also be prefilled with pharmaceutical compositions comprising antagonistic human monoclonal antibodies against human IL-17 Receptor A. The characterization, cloning, and preparation of IL-17 Receptor A are described in U.S. Pat. No. 6,072,033, issued Jun. 6, 2000, which is incorporated herein by reference in its entirety. The amino acid sequence of the human IL-17RA is shown in SEQ ID NO:10 of U.S. Pat. No. 6,072,033 (GenBank accession number NM_014339). Such antibodies may comprise those disclosed in WO 2008/054603, which is incorporated by reference in its entirety or the antibodies claimed in U.S. Pat. No. 7,767,206, issued Aug. 3, 2010, and in U.S. Ser. No. 11/906,094, which are incorporated by reference in their entirety.

The syringe or other primary container of the AI may also be prefilled with IFN gamma specific antibodies, peptibodies, and related proteins and the like, especially human IFN gamma specific antibodies, particularly fully human anti-IFN gamma antibodies, such as, for instance, those described in US Publ. No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Publication and in Thakur et al., Mol. Immunol. 36:1107-1115 (1999). In addition, description of the properties of these antibodies provided in the foregoing US publication is also incorporated by reference herein in its entirety. Specific antibodies comprise those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein.

The syringe or other primary container of the AI may also be prefilled with TALL-1 specific antibodies, peptibodies, and related proteins, and the like, and other TALL specific binding proteins, such as those described in U.S. Publ. Nos. 2003/0195156 and 2006/0135431, each of which is incorporated herein by reference in its entirety as to TALL-1 binding proteins, particularly the molecules of Tables 4 and 5B therein, each of which is individually and specifically incorporated by reference herein in its entirety fully as disclosed in the foregoing US Publications.

The syringe or other primary container of the AI may also be prefilled with PTH specific antibodies, peptibodies, and related proteins, and the like, such as those described in U.S. Pat. No. 6,756,480, which is incorporated herein by reference in its entirety, particularly in parts pertinent to proteins that bind PTH.

The syringe or other primary container of the AI may also be prefilled with TPO-R specific antibodies, peptibodies, and related proteins, and the like, such as those described in U.S. Pat. No. 6,835,809, which is herein incorporated by reference in its entirety, particularly in parts pertinent to proteins that bind TPO-R.

The syringe or other primary container of the AI may also be prefilled with HGF specific antibodies, peptibodies, and related proteins, and the like, comprising those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, each of which is incorporated herein by reference in its entirety, particularly in parts pertinent to proteins that bind HGF.

The syringe or other primary container of the AI may also be prefilled with TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2.

The syringe or other primary container of the AI may also be prefilled with Activin A specific antibodies, peptibodies, related proteins, and the like, comprising but not limited to those described in US Publ. No. 2009/0234106, which is herein incorporated by reference in its entirety, particularly in parts pertinent to proteins that bind Activin A.

The syringe or other primary container of the AI may also be prefilled with TGF-beta specific antibodies, peptibodies, related proteins, and the like, comprising but not limited to those described in U.S. Pat. No. 6,803,453 and US Publ. No. 2007/0110747, each of which is herein incorporated by reference in its entirety, particularly in parts pertinent to proteins that bind TGF-beta.

The syringe or other primary container of the AI may also be prefilled with amyloid-beta protein specific antibodies, peptibodies, related proteins, and the like, comprising but not limited to those described in PCT Publ. No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication.

The syringe or other primary container of the AI may also be prefilled with c-Kit specific antibodies, peptibodies, related proteins, and the like, comprising but not limited to those described in Publ. No. 2007/0253951, which is incorporated herein by reference in its entirety, particularly in parts pertinent to proteins that bind c-Kit and/or other stem cell factor receptors.

The syringe or other primary container of the AI may also be prefilled with OX40L specific antibodies, peptibodies, related proteins, and the like, comprising but not limited to those described in U.S. application Ser. No. 11/068,289, which is incorporated herein by reference in its entirety, particularly in parts pertinent to proteins that bind OX40L and/or other ligands of the OXO40 receptor.

The syringe or other primary container of the AI may also be prefilled with other exemplary proteins comprising but are not limited to Activase® (Alteplase, tPA); Aranesp® (Darbepoetin alfa), Epogen® (Epoetin alfa, or erythropoietin); Avonex® (Interferon beta-1a); Bexxar® (Tositumomab, anti-CD22 monoclonal antibody); Betaseron® (Interferon-beta); Campath® (Alemtuzumab, anti-CD52 monoclonal antibody); Dynepo® (Epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (Epoetin alfa); Erbitux® (Cetuximab, anti-EGFR/HER1/c-ErbB-1); Genotropin® (Somatropin, Human Growth Hormone); Herceptin® (Trastuzumab, anti-HER2/neu (erbB2) receptor mAb); Humatrope® (Somatropin, Human Growth Hormone); Humira® (Adalimumab); Insulin in Solution; Infergen® (Interferon Alfacon-1); Natrecor® (nesiritide; recombinant human B-type natriuretic peptide (hBNP); Kineret® (Anakinra), Leukine® (Sargamostim, rhuGM-CSF); LymphoCide® (Epratuzumab, anti-CD22 mAb); Lymphostat B® (Belimumab, anti-BlyS mAb); Metalyse® (Tenecteplase, t-PA analog); Mircera® (methoxy polyethylene glycol-epoetin beta); Mylotarg® (Gemtuzumab ozogamicin); Raptiva® (efalizumab); Cimzia® (certolizumab pegol, CDP 870); Soliris™ (Eculizumab); Pexelizumab (Anti-C5 Complement); MEDI-524 (Numax®); Lucentis® (Ranibizumab); 17-1A (Edrecolomab, Panorex®); Trabio® (lerdelimumab); TheraCim hR3 (Nimotuzumab); Omnitarg (Pertuzumab, 2C4); Osidem® (IDM-1); OvaRex® (B43.13); Nuvion® (visilizumab); Cantuzumab mertansine (huC242-DM1); NeoRecormon® (Epoetin beta); Neumega® (Oprelvekin, Human Interleukin-11); Neulasta® (Pegylated filgastrim, pegylated G-CSF, pegylated hu-Met-G-CSF); Neupogen® (Filgrastim, G-CSF, hu-MetG-CSF); Orthoclone OKT3® (Muromonab-CD3, anti-CD3 monoclonal antibody), Procrit® (Epoetin alfa); Remicade® (Infliximab, anti-TNFα monoclonal antibody), Reopro® (Abciximab, anti-GP IIb/Ilia receptor monoclonal antibody), Actemra® (anti-IL6 Receptor mAb), Avastin® (Bevacizumab), HuMax-CD4 (zanolimumab), Rituxan® (Rituximab, anti-CD20 mAb); Tarceva® (Erlotinib); Roferon-A®-(Interferon alfa-2a); Simulect® (Basiliximab); Prexige® (lumiracoxib); Synagis® (Palivizumab); 146B7-CHO (anti-IL15 antibody, see U.S. Pat. No. 7,153,507), Tysabri® (Natalizumab, anti-α4integrin mAb); Valortim® (MDX-1303, anti-*B. anthracis* Protective Antigen mAb); ABthrax™; Vectibix® (Panitumumab); Xolair® (Omalizumab), ETI211 (anti-MRSA mAb), IL-1 Trap (the Fc portion of human IgG1 and the extracellular domains of both IL-1 receptor components (the Type I receptor and receptor accessory protein)), VEGF Trap (Ig domains of VEGFR1 fused to IgG1 Fc), Zenapax® (Daclizumab); Zenapax® (Daclizumab, anti-IL-2Rα mAb), Zevalin® (Ibritumomab tiuxetan), Zetia (ezetimibe), Atacicept (TACI-Ig), anti-CD80 monoclonal antibody (mAb) (galiximab), anti-CD23 mAb (lumiliximab). BR2-Fc (huBR3/huFc fusion protein, soluble BAFF antagonist); CNTO 148 (Golimumab, anti-TNFα mAb); HGS-ETR1 (Mapatumumab; human anti-TRAIL Receptor-1 mAb); HuMax-CD20 (Ocrelizumab, anti-CD20 human mAb); HuMax-EGFR (zalutumumab); M200 (Volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL 12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2; a sclerostin antibody, such as but not limited to romosozumab, blosozumab, or BPS 804 (Novartis). Also included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the AI can be a monoclonal antibody (IgG) that binds human Proprotein Convertase Subtilisin/Kexin Type 9 (PCSK9), e.g. U.S. Pat. No. 8,030,547, U.S. Ser. No. 13/469,032, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

The syringe or other primary container of the AI may also be prefilled with antibodies comprising, but not limited to, those that recognize any one or a combination of proteins comprising, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β. IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1): 19-25), C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, Respiratory Syncitial Virus, human immunodeficiency virus (HIV), hepatitis B virus (HBV), Streptococcus mutans, and Staphlycoccus aureus.

Additional examples of known antibodies that may be contained in the syringe or other primary container of the AI can comprise but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, zalutumumab, and zanolimumab.

Although the SMF, the palm button, the HH device, the needle shield, and the AI device have been described in terms of illustrative embodiments, they are not limited thereto. Rather, the appended claims should be construed broadly, to comprise other variants and embodiments of the SMF, the palm button, the HH device, the needle shield, and the AI device, which may be made by those skilled in the art without departing from the scope and range of equivalents of the SMF, the palm button, the HH device, the needle shield, and the AI device and their elements.

What is claimed is:

1. An injector comprising:

a housing having an activation end and an injection end disposed opposite to and inline with the activation end; and a palm button device disposed at the activation end of the housing, the palm button device depressible to allow activation of the injector with the palm of an operator's hand, the palm button device comprising:

a palm-operated button having a surface which is sized and configured for accommodating the palm of the operator's hand;

a mounting arrangement for operatively coupling the device to the activation end of the housing of the injector, the mounting arrangement comprising a base extending from the palm-operated button and an adaptor slidably coupled to the base, the adaptor surrounding only a portion of the housing at the activation end; and a biasing device causing activation of the injector when the palm-operated button is moved to a depressed position and independently returning the palm-operated button from the depressed position to an undepressed position using stored energy of the biasing device.

2. The injector according to claim 1, wherein the palm-operated button has a hemispherical-shape.

3. The injector according to claim 1, wherein the palm-operated button has a T-shaped handle.

4. The injector according to claim 1, wherein the palm-operated button has at least one indent for placement of a user's thumb.

5. The injector according to claim 1, wherein the palm-operated button has a polyurethane gel elastomer coating.

6. The injector according to claim 1, wherein the palm button device is removably attached to the housing of the injector.

7. The injector according to claim 1, wherein the palm button device is non-removably attached to the housing of the injector.

8. The injector according to claim 1, wherein the operation of the palm button device arms the injector.

9. An injector comprising:

a housing; and a holding device for aiding a user in the operation of the injector, the holding device comprising:

a sleeve for ergonomically holding and operating the injector with one hand, the sleeve including a slot having a lateral edge surface, a recess formed in the lateral edge surface of the slot; and at least one hand rest including a concave surface extending out from the sleeve for maintaining a user's hand on the sleeve when holding and operating the injector, wherein the concave surface of the at least one hand rest extending out from the sleeve is contoured to receive the hypothenar muscle area of the user's hand, wherein the at least one hand rest is pivotally coupled to the sleeve by a pivot pin structure located within the sleeve such that the concave surface rotates from a position facing the sleeve to an upward facing position as a result of the at least one hand rest pivoting around the pivot pin structure, the concave surface in the upward facing position as the injector is activated, wherein the at least one hand rest includes a projection that slidably engages the lateral edge surface of the slot and enters the recess in a clamping position.

10. The injector according to claim 9, wherein the sleeve of the holding device has a polyurethane gel elastomer layer that defines a hand grip.

11. The injector according to claim 9, wherein the sleeve has a top wall operative as stop for properly positioning the sleeve on the injector so that a user can operate the injector with one hand.

12. The injector according to claim 11, wherein the top wall includes an opening for allowing an activation button of the injector to extend through the top wall.

13. The injector according to claim 9, wherein the holding device is removably attached to the housing of the injector.

14. The injector according to claim 9, wherein the holding device includes a locking arrangement for non-removably attaching the holding device to the housing of the injector.

15. The injector according to claim 9, wherein the holding device allows a user to arm and/or initiate the injection cycle of the injector.

16. The injector according to claim 9, wherein the sleeve is capable of being slidably moved on the housing of the injector to initiate the injection cycle of the injector.

* * * * *